(12) United States Patent
Tada et al.

(10) Patent No.: US 8,779,174 B2
(45) Date of Patent: Jul. 15, 2014

(54) TITANIUM COMPLEX, PROCESSES FOR PRODUCING THE SAME, TITANIUM-CONTAINING THIN FILM, AND PROCESS FOR PRODUCING THE SAME

(75) Inventors: Ken-ichi Tada, Kanagawa (JP); Toshiki Yamamoto, Kanagawa (JP); Hirokazu Chiba, Kanagawa (JP); Kohei Iwanaga, Kanagawa (JP); Atsushi Maniwa, Kanagawa (JP); Tadahiro Yotsuya, Kanagawa (JP); Noriaki Oshima, Kanagawa (JP)

(73) Assignees: Tosoh Corporation, Yamaguchi (JP); Sagami Chemical Research Institute, Kanagawa (JP)

( * ) Notice: Subject to any disclaimer, the term of this patent is extended or adjusted under 35 U.S.C. 154(b) by 324 days.

(21) Appl. No.: 12/996,690

(22) PCT Filed: Jun. 12, 2009

(86) PCT No.: PCT/JP2009/060801
§ 371 (c)(1),
(2), (4) Date: Dec. 7, 2010

(87) PCT Pub. No.: WO2009/157326
PCT Pub. Date: Dec. 30, 2009

(65) Prior Publication Data
US 2012/0029220 A1 Feb. 2, 2012

(30) Foreign Application Priority Data
Jun. 23, 2008 (JP) ................................. 2008-163477

(51) Int. Cl.
*C07F 7/28* (2006.01)

(52) U.S. Cl.
USPC .......................................................... 556/56

(58) Field of Classification Search
None
See application file for complete search history.

(56) References Cited

U.S. PATENT DOCUMENTS

| | | | |
|---|---|---|---|
| 5,866,205 A | 2/1999 | Vaartstra et al. | |
| 7,632,958 B2 * | 12/2009 | Tada et al. | 556/51 |
| 2009/0036697 A1 | 2/2009 | Tada et al. | |

FOREIGN PATENT DOCUMENTS

JP 2007-153872 A 6/2007

OTHER PUBLICATIONS

Hans Joachim Rieger, "Synthesen, Reaktionen und Strukturen von 1,4-Diaza-1,3-butadien (DAD)-Komplexen des Ti, Ba, Y und Anwendung von DADTi-Komplexen zur Anscheidung von Titan-Nitrid-Schichten uber das R-PECVD-Verfahren", Hamburg 1992, 70 pages total.

Kim, J.Y. et., al. "Characteristics and Compositional Variation of TiN Films Deposited by Remote PEALD on Contact Holes", Journal of the Electrochemical Society, No. 152, 2005, pp. G29-G34.

Jones, A. C. et., al. "Synthesis and characterisation of two novel titanium isopropoxides stabilised with chelating alkoxide: their use in liquid injection MOCVD of titanium dioxide thin films", Journal of Materials Chemistry, 1998, No. 8, pp. 1773-1777.

Lee, J. P. et., al. "Atomic Layer Deposition of $TiO_2$ Thin Films from $Ti(O^iPr)_2(dmae)_2$ and $H_2O$", Bull. Korean Chemical Soc., 2004, vol. 25, No. 4, pp. 475-479.

Pheamhom, R. et., al. "Characteristics of atomic layer deposited $TiO_2$ films and their photocatalytic activity", J. Vac. Sci. Technol., vol. 24, No. 4, Jul./Aug. 2006. 99. 1535-1539.

Besserguenev, V. G. et., al. "$TiO_2$ thin film synthesis from complex precursors by CVD, its physical and photocatalytic properties" International Journal of Photoenergy, vol. 5, 2003, pp. 99-105.

Bhakta, R. et., al. "MOCVD of $TiO_2$ thin films and studies on the nature of molecular mehanisms involved in the decomposition of $[Ti(OPr^j)_2(tbaoac)_2]$", Journal of Materials Chemistry, 2004, vol. 14, pp. 3231-3238.

Chamberlain, L. et., al. "Intramolecular Coupling of $\eta^2$-Iminoacyl and $\eta^2$-Acyl Functions at Group 4 and Group 5 Metal Centers: Structure and Enediamide Complexes", Journal of American Chemical Society, 1987, vol. 109(20), pp. 6068-6076.

Galindo, A. et., al. "Folded 2,5-diazapent-3-ene metallacycle in enediamido group 4 metal compounds: DFT and AIM analyses", Journal of Organometallic Chemistry, 2004, 689(18), pp. 2847-2852.

International Search Report for PCT/JP2009/060801 dated Jul. 21, 2009 [PCT/ISA/210].

(Continued)

*Primary Examiner* — Sudhakar Katakam
(74) *Attorney, Agent, or Firm* — Sughrue Mion, PLLC

(57) ABSTRACT

A subject for the invention is to provide novel titanium complexes which have a high vapor pressure and high thermal stability and serve as an excellent material for producing a titanium-containing thin film by a technique such as the CVD method or ALD method and to further provide processes for producing these complexes, titanium-containing thin films produced from the complexes, and a process for producing the thin films. The invention relates to producing a titanium complex represented by general formula (1):

[Chem. 1] (1)

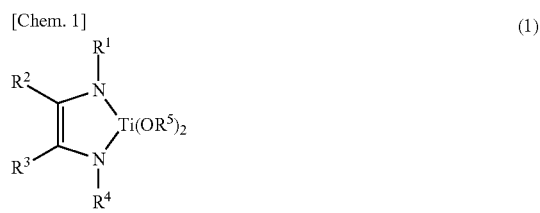

(wherein $R^1$ and $R^4$ each independently represent an alkyl group having 1-16 carbon atoms; $R^2$ and $R^3$ each independently represent a hydrogen atom or an alkyl group having 1-3 carbon atoms; and $R^5$ represents an alkyl group which has 1-16 carbon atoms and may have been substituted with one or more fluorine atoms) and to producing a titanium-containing thin film using the complex.

7 Claims, 8 Drawing Sheets

(56) References Cited

OTHER PUBLICATIONS

Frenck, H. J. et al. "Application and Possibilities of the Remote PECVD Process to Deposition of Thin Nitride Films from Metalorganic Sources." ISPC-10 Bochum, Aug. 1991. 2.4-28. p. 1-6.
H.J.Frenck, et al., IPAT 91, p. 30-35 (8th International Conference Ion & Plasma Assisted Techniques, Brussels, May 1991).
Communication dated May 10, 2013 from the Taiwanese Patent Office in counterpart Taiwanese application No. 098120854.
Heindirk et al., "Diazadiene complexes of Group 4 metals I. Synthesis of mono-, bis- and tris(diazadiene) titanium complexes and the structure of diazadienedichlorotitanium", Inorganica Chimica Acta, received Jun. 8, 1990, 177, pp. 191-197.
Office Action dated Feb. 5, 2013, issued by The Patent Office of the People's Republic of China in counterpart Chinese Patent Application No. 200980123896.X.
Office Action, dated Sep. 10, 2013, issued by the State Intellectual Property Office of the People's Republic of China in counterpart Chinese Application No. 200980123896.X.

* cited by examiner

TITANIUM COMPLEX, PROCESSES FOR PRODUCING THE SAME, TITANIUM-CONTAINING THIN FILM, AND PROCESS FOR PRODUCING THE SAME

TECHNICAL FIELD

The present invention relates to a titanium complex useful as a raw material for producing semiconductor elements, processes for producing the complex, a titanium-containing thin film, and a process for producing the thin film.

BACKGROUND ART

At present, it is required to highly integrate semiconductor elements in order to promote performance advancement in semiconductor devices such as random access memories and flash memories. For attaining the high degree of integration of semiconductor elements, it is essential that a technique for forming a thin film having an even thickness on the surface of a fine three-dimensional structure should be established and put to practical use. The CVD method, in which a gaseous material is decomposed on a substrate to deposit a film, or the atomic layer deposition method (ALD method), in which a material adsorbed on a substrate surface is decomposed to deposit a film, is attracting attention as a promising candidate for that technique. Investigations are presently being made in order to put these techniques into practical use.

Substances having a high vapor pressure and thermal stability are selected as materials to be used for forming a thin film by the CVD method or ALD method. For forming thin films of constant quality, it is important to precisely control the concentration of the material during thin-film formation. From this standpoint, liquid materials are preferred materials for thin-film formation because the rate of vaporization thereof is easier to control than that of solid materials.

Titanium oxide and titanium-containing oxides are regarded as candidates for materials for the capacitor dielectric films of next-generation and succeeding dynamic random access memories (DRAMs). Titanium-containing oxides are regarded also as a candidate for, for example, a material for the ferroelectric film of a non-volatile memory.

Titanium tetrachloride $TiCl_4$, tetraisopropoxotitanium $Ti(O^iPr)_4$, and the like have been investigated hitherto as materials for forming a titanium-containing thin film by the CVD method or the ALD method.

Some attempts have been made to incorporate a chelate ligand in order to control the reactivity of $Ti(O^iPr)_4$ with water. For example, titanium compounds having one or more chelate ligands, such as (diisopropoxo)(bis(2,2,6,6-tetramethylheptanedionato))titanium $(Ti(O^iPr)_2(THD)_2)$, diisopropoxobis(tert-butylacetoacetato)titanium $(Ti(O^iPr)_2(tbaoac)_2)$, bis(dimethylaminoethoxo)-diisopropoxotitanium $(Ti(O^iPr)_2(dmae)_2)$, and (dimethylaminoethoxo)triisopropoxo-titanium $(Ti(O^iPr)_3(dmae))$, have been synthesized and are being investigated as materials for use in the CVD method or the ALD method. (Non-patent documents 1, 2, 3, and 4).

Furthermore, titanium compounds having amide ligands are also being investigated as materials for forming a thin film by the CVD method or the ALD method. For example, formation of a thin titanium nitride film, thin titanium oxide film, or the like by the CVD method or ALD method using tetrakis (dimethylamido)titanium $(Ti(NMe_2)_4)$ as a material is being investigated. (For example, non-patent documents 5 and 6). Amidotitanium complexes having a chelate ligand are also being investigated as materials for thin-film formation. Examples thereof include the titanium complexes described in patent document 1.

Moreover, an aryloxo complex which is similar in structure to the titanium complex of the present invention because of the possession of an ethene-1,2-diyldiamide ligand is known. (Non-patent document 7)

PRIOR-ART DOCUMENTS

Patent Document

Patent Document 1: JP-A-2007-153872

Non-Patent Documents

Non-Patent Document 1: *International Journal of Photoenergy*, Vol. 5, p. 99 (2003)
Non-Patent Document 2: *Journal of Materials Chemistry*, Vol. 14, p. 3231 (2004)
Non-Patent Document 3: *Bulletin of the Korean Chemical Society*, Vol. 25, p. 475 (2004)
Non-Patent Document 4: *Journal of Materials Chemistry*, Vol. 8, p. 1773 (1998)
Non-Patent Document 5: *Journal of Vacuum Science & Technology A*, Vol. 24, p. 1535 (2006)
Non-Patent Document 6: *Journal of the Electrochemical Society*, Vol. 152, p. G29 (2005)
Non-Patent Document 7: *Journal of the American Chemical Society*, Vol. 109, p. 6068 (1987)

SUMMARY OF THE INVENTION

Problems that the Invention is to Solve $TiCl_4$ has problems, for example, that a high temperature is necessary for film deposition therefrom and that thin films formed therefrom contain chlorine. $Ti(O^iPr)_4$ has exceedingly high reactivity with water and readily reacts with the water contained in a slight amount in, for example, a carrier gas or reactant gas used in film deposition. As a result, a fine powder of titanium oxide is formed in the piping within the apparatus and there is a possibility that this fine powder might clog the apparatus to reduce productivity. Meanwhile, the chelate-coordination titanium complexes described in non-patent documents 1, 2, 3, and 4 have a drawback that the titanium complexes have a low vapor pressure. Furthermore, $Ti(NMe_2)_4$ has exceedingly high reactivity with water and reacts with the water contained in a slight amount in, for example, a carrier gas or reactant gas used in film deposition. There is hence a possibility that the resultant reaction product might clog the apparatus to reduce productivity as in the case of $Ti(O^iPr)_4$.

The aryloxo complex described in non-patent document 7 differs in having a plurality of bulky aryl groups from the titanium complex of the present invention. Furthermore, the aryloxo complex synthesis method described in non-patent document 7 differs from the production processes of the invention. In addition, in non-patent document 7, there is no statement concerning use of the aryloxo complex as a material for titanium-containing thin films.

The titanium complexes described in patent document 1 combine thermal stability and vapor pressure which render the complexes suitable for use as a material in the CVD method or ALD method. However, there recently is a desire for the development of a material having higher thermal stability than those titanium complexes.

An object of the invention is to provide novel titanium complexes which have a high vapor pressure and high thermal stability and serve as an excellent material for producing a titanium-containing thin film by a technique such as the CVD method or the ALD method and to further provide processes for producing these complexes, titanium-containing thin films produced from the complexes, and a process for producing the thin films.

Means for Solving the Problems

In view of the current circumstances described above, the present inventors diligently made investigations. As a result, they have found that a titanium complex represented by general formula (1) is an excellent compound capable of eliminating the problems described above. The invention has been thus completed.

Namely, the invention provides a titanium complex represented by general formula (1):

[Chem. 1]

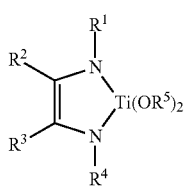

(1)

(wherein $R^1$ and $R^4$ each independently represent an alkyl group having 1-16 carbon atoms; $R^2$ and $R^3$ each independently represent a hydrogen atom or an alkyl group having 1-3 carbon atoms; and $R^5$ represents an alkyl group which has 1-16 carbon atoms and may have been substituted with one or more fluorine atoms).

The invention further provides a process for producing a titanium complex represented by general formula (1), characterized by subjecting a diimine represented by general formula (2):

[Chem. 2]

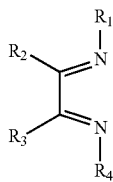

(2)

(wherein $R^1$ and $R^4$ each independently represent an alkyl group having 1-16 carbon atoms, and $R^2$ and $R^3$ each independently represent a hydrogen atom or an alkyl group having 1-3 carbon atoms), an alkali metal, and an alkoxo complex represented by general formula (3):

[Chem. 3]

$Ti(OR^5)_4$ (3)

(wherein $R^5$ represents an alkyl group which has 1-16 carbon atoms and may have been substituted with one or more fluorine atoms) to reaction with one another.

The invention furthermore provides a process for producing a titanium complex represented by general formula (1a):

[Chem. 6]

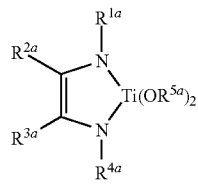

(1a)

(wherein $R^{1a}$ and $R^{4a}$ each independently represent an alkyl group having 1-6 carbon atoms; $R^{2a}$ and $R^{3a}$ each independently represent a hydrogen atom or an alkyl group having 1-3 carbon atoms; and $R^{5a}$ represents an alkyl group which has 1-16 carbon atoms and may have been substituted with one or more fluorine atoms), characterized by subjecting an alcohol represented by general formula (5):

[Chem. 5]

$R^{5a}OH$ (5)

(wherein $R^{5a}$ represents an alkyl group which has 1-16 carbon atoms and may have been substituted with one or more fluorine atoms) to reaction with an amide complex represented by general formula (4):

[Chem. 4]

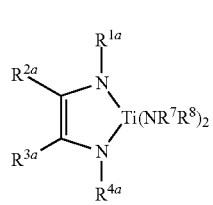

(4)

(wherein $R^{1a}$ and $R^{4a}$ each independently represent an alkyl group having 1-6 carbon atoms; $R^{2a}$ and $R^{3a}$ each independently represent a hydrogen atom or an alkyl group having 1-3 carbon atoms; and $R^7$ and $R^8$ each independently represent an alkyl group which has 1-4 carbon atoms and may have been substituted with one or more fluorine atoms).

The invention still further provides a titanium-containing thin film produced by using a titanium complex represented by general formula (1) as a material.

The invention still further provides a process for producing a titanium-containing thin film, characterized by using a titanium complex represented by general formula (1) as a material.

The invention still further provides a semiconductor device characterized by using the titanium-containing thin film described above.

The invention still further provides a photocatalyst characterized by using the titanium-containing thin film described above.

Advantages of the Invention

The titanium complex (1) of the invention has satisfactory vaporization characteristics and excellent thermal stability, namely, has a high vapor pressure and high thermal stability.

A titanium-containing thin film can hence be produced by a technique, such as the CVD method or ALD method, using the complex as a material.

MODES FOR CARRYING OUT THE INVENTION

Figure 1:
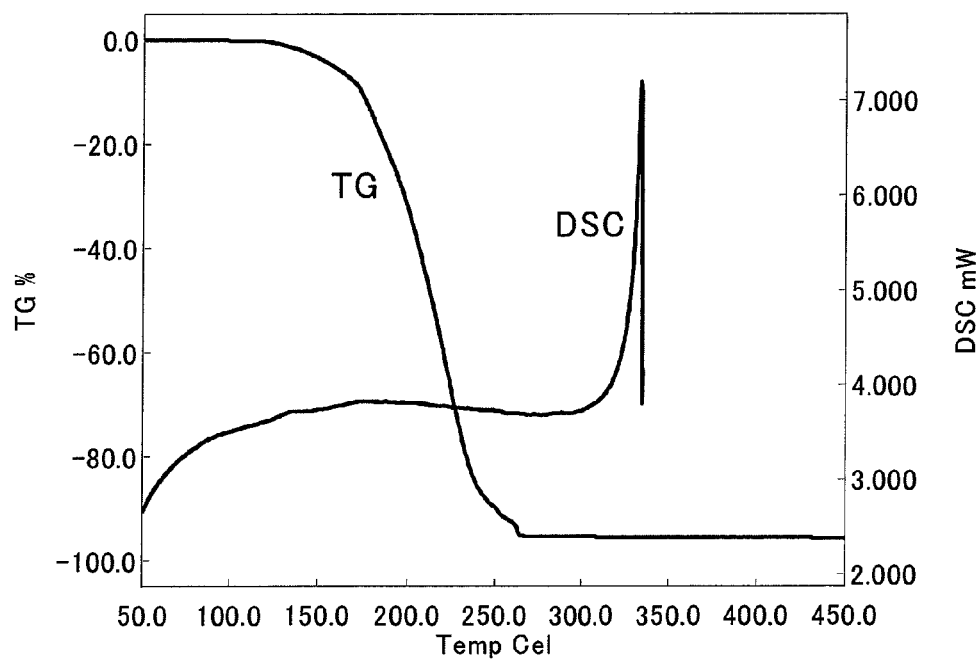
FIG. 1 is a presentation showing the results of the TG and DSC analyses conducted in Test Example 1.

The invention will be explained below in more detail.
Examples of the alkyl groups having 1-16 carbon atoms which are represented by $R^1$ and $R^4$ include methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, 1-ethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, cyclopropyl, cyclobutyl, cyclopentyl, cyclohexyl, cyclopropylmethyl, cyclopropylethyl, cyclobutylmethyl, heptyl, cyclohexylmethyl, 1,1-diethylpropyl, 2-methylcyclohexyl, 4-methylcyclohexyl, octyl, 1,1-diethyl-2-methylpropyl, 2,5-dimethylcyclohexyl, 3,5-dimethylcyclohexyl, 1,1,3,3-tetramethylbutyl, 1-methyl-1-propylbutyl, 1,1,2,3,3-pentamethylbutyl, 1,1-diethyl-3,3-dimethylbutyl, adamantyl, 1,1-dimethyloctyl, 1,1-dipropylbutyl, 1,1-dimethyldecyl, 1,1-diethyloctyl, 1,1-dibutylpentyl, 1,1-dibutylhexyl, 1,1-dibutylheptyl, or 1,1-dipentylhexyl.

Examples of the alkyl groups having 1-3 carbon atoms which are represented by $R^2$ and $R^3$ include methyl, ethyl, propyl, isopropyl, or cyclopropyl.

Examples of the alkyl group having 1-16 carbon atoms which is represented by $R^5$ include methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, 1-ethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, cyclopropyl, cyclobutyl, cyclopentyl, cyclohexyl, cyclopropylmethyl, cyclopropylethyl, cyclobutylmethyl, heptyl, cyclohexylmethyl, 1,1-diethylpropyl, 2-methylcyclohexyl, 4-methylcyclohexyl, octyl, 1,1-diethyl-2-methylpropyl, 2,5-dimethylcyclohexyl, 3,5-dimethylcyclohexyl, 1,1,3,3-tetramethylbutyl, 1-methyl-1-propylbutyl, 1,1,2,3,3-pentamethylbutyl, 1,1-diethyl-3,3-dimethylbutyl, adamantyl, 1,1-dimethyloctyl, 1,1-dipropylbutyl, 1,1-dimethyldecyl, 1,1-diethyloctyl, 1,1-dibutylpentyl, 1,1-dibutylhexyl, 1,1-dibutylheptyl, or 1,1-dipentylhexyl.

These alkyl groups may have been substituted with fluorine atoms. Examples of such groups include trifluoromethyl, 2,2,2-trifluoroethyl, perfluoroethyl, perfluoropropyl, perfluoroisopropyl, perfluorobutyl, perfluoro-sec-butyl, perfluoro-tert-butyl, perfluorohexyl, perfluoroheptyl, perfluorooctyl, perfluorononyl, perfluorodecyl, perfluoroundecyl, perfluorododecyl, perfluorotridecyl, perfluorotetradecyl, perfluoropentadecyl, or perfluorohexadecyl.

From the standpoint of imparting a satisfactory vapor pressure and excellent thermal stability, it is preferred that $R^1$ and $R^4$ in the titanium complex (1) should each independently be an alkyl group having 2-6 carbon atoms. Preferred are, for example, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, 1-ethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, cyclopropyl, cyclobutyl, cyclopentyl, cyclohexyl, cyclopropylmethyl, cyclopropylethyl, and cyclobutylmethyl. It is more preferred that $R^1$ and $R^4$ should each independently be an alkyl group having 4 or 5 carbon atoms. For example, $R^1$ and $R^4$ more preferably are butyl, isobutyl, sec-butyl, tert-butyl, pentyl, isopentyl, neopentyl, tert-pentyl, 1-methylbutyl, 2-methylbutyl, 1,2-dimethylpropyl, or 1-ethylpropyl.

$R^2$ and $R^3$ preferably are hydrogen atoms.

It is preferred that $R^5$ should be an alkyl group having 1-8 carbon atoms. For example, $R^5$ preferably is methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, 1-ethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, cyclopropyl, cyclobutyl, cyclopentyl, cyclohexyl, cyclopropylmethyl, cyclopropylethyl, cyclobutylmethyl, heptyl, cyclohexylmethyl, 1,1-diethylpropyl, 2-methylcyclohexyl, 4-methylcyclohexyl, octyl, 1,1-diethyl-2-methylpropyl, 2,5-dimethylcyclohexyl, 3,5-dimethylcyclohexyl, 1,1,3,3-tetramethylbutyl, or 1-methyl-1-propylbutyl. It is more preferred that $R^5$ should be an alkyl group having 3-5 carbon atoms. For example, $R^5$ more preferably is propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, or 1-ethylpropyl.

The titanium complex represented by general formula (1) preferably is ethene-1,2-diylbis(isopropylamido)bis(tert-pentyloxo)titanium (Ti($^i$PrNCHCHN$^i$Pr)(O$^t$Pe)$_2$), ethene-1,2-diylbis(tert-butylamido)diethoxotitanium (Ti($^t$BuNCHCHN$^t$Bu)(OEt)$_2$), ethene-1,2-diylbis(tert-butylamido)diisopropoxotitanium (Ti($^t$BuNCHCHN$^t$Bu)(O$^i$Pr)$_2$), ethene-1,2-diylbis(tert-butylamido)bis(tert-pentyloxo)titanium (Ti($^t$BuNCHCHN$^t$Bu)(O$^t$Pe)$_2$), ethene-1,2-diylbis(tert-butylamido)bis(1,1-diethylpropyloxo)titanium (Ti($^t$BuNCHCHN$^t$Bu)(OCEt$_3$)$_2$), ethene-1,2-diylbis(tert-butylamido)bis(1,1-diethyl-2-methylpropyloxo)titanium (Ti($^t$BuNCHCHN$^t$Bu)(OCEt$_2$CHMe$_2$)$_2$), ethene-1,2-diylbis(tert-butylamido)bis(2,2,2-trifluoroethoxo)titanium (Ti($^t$BuNCHCHN$^t$Bu)(OCH$_2$CF$_3$)$_2$), ethene-1,2-diylbis(tert-pentylamido)dimethoxotitanium (Ti($^t$PeNCHCHN$^t$Pe)(OMe)$_2$), ethene-1,2-diylbis(tert-pentylamido)diethoxotitanium (Ti($^t$PeNCHCHN$^t$Pe)(OEt)$_2$), ethene-1,2-diylbis(tert-pentylamido)diisopropoxotitanium (Ti($^t$PeNCHCHN$^t$Pe)(O$^i$Pr)$_2$), ethene-1,2-diylbis(tert-pentylamido)di(tert-butoxo)titanium (Ti($^t$PeNCHCHN$^t$Pe)(O$^t$Bu)$_2$), or ethene-1,2-diylbis(1,1,3,3-tetramethylbutylamido)diisopropoxotitanium (Ti(Me$_3$CCH$_2$CMe$_2$NCHCHNCMe$_2$CH$_2$CMe$_3$)(O$^i$Pr)$_2$), from the standpoint that these titanium complexes have a satisfactory vapor pressure and excellent thermal stability. More preferred examples thereof include ethene-1,2-diylbis(tert-butylamido)diisopropoxotitanium (Ti($^t$BuNCHCHN$^t$Bu)(O$^i$Pr)$_2$), ethene-1,2-diylbis(tert-butylamido)bis(tert-pentyloxo)titanium (Ti($^t$BuNCHCHN$^t$Bu)(O$^t$Pe)$_2$), or ethene-1,2-diylbis(tert-pentylamido)diisopropoxotitanium (Ti($^t$PeNCHCHN$^t$Pe)(O$^i$Pr)$_2$).

The production processes of the invention are explained next. Production process 1 is a process in which an alkali metal and the alkoxo complex (3) are subjected to reaction with the diimine (2) in an organic solvent to thereby produce a titanium complex (1) of the invention.

The diimine (2) to be used as a starting material can be synthesized with reference to a known method (e.g., *Journal of the American Chemical Society*, Vol. 120, p. 12714 (1998)). Besides being available as a commercial reagent or industrial material, the alkoxo complex (3) can be synthesized with reference to *Journal of the American Chemical Society*, Vo. 46, p. 256 (1924), *Inorganica Chimica Acta*, Vol. 52, p. 79 (1981), and *Alkoxo and Aryloxo Derivatives of Metals*, Academic Press (2001).

It is known that subjecting the diimine (2) to reaction with an alkali metal yields an alkali metal complex of the diimine (for example, *Journal of the American Chemical Society*, Vol. 120, p. 12714 (1998)). In production process 1 of the invention, the order of reaction of the diimine (2), alkali metal, and alkoxo complex (3) is not limited. For example, the alkoxo complex (3) may be subjected to reaction with the alkali metal complex of the diimine, which has been prepared separately and isolated. It is preferred that an alkali metal should be first subjected to reaction with the diimine (2) and the alkoxo complex (3) be subsequently subjected to reaction, from the standpoint that this method involves a smaller number of steps and a titanium complex (1) is obtained in satisfactory yield.

It is preferred that the kind of the alkali metal to be used in production process 1 should be lithium or sodium from the standpoint of obtaining the titanium complex (1) in satisfactory yield. It is preferred that the alkali metal should be used in an amount of at least 2 equivalents to the diimine from the standpoint of obtaining the titanium complex (1) in satisfactory yield. The organic solvent to be used in production process 1 may be any organic solvent which does not react with the alkali metal, the diimine (2), the alkoxo complex (3), and an alkali metal complex of the diimine (2). Examples thereof include alkanes such as pentane, hexane, heptane, octane, cyclohexane, methylcyclohexane, and ethylcyclohexane, aromatic hydrocarbons such as benzene, toluene, and xylene, and ethers such as diethyl ether, diisopropyl ether, dibutyl ether, tetrahydrofuran, dioxane, ethylene glycol dimethyl ether, diglyme, triglyme, and cyclopentyl methyl ether. These may be used alone or as a mixture thereof.

The titanium complex (1) of the invention obtained by production process 1 can be isolated by using suitably selected general techniques for purification of complexes, such as filtration, extraction, distillation, sublimation, and crystallization.

Production process 2 is a process in which the alcohol (5) is subjected to reaction with the amide complex (4) in an organic solvent to thereby produce a titanium complex (1a).

In the invention, examples of the alkyl groups having 1-6 carbon atoms which are represented by $R^{1a}$ and $R^{4a}$ include methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, 1-ethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, cyclopropyl, cyclobutyl, cyclopentyl, cyclohexyl, cyclopropylmethyl, cyclopropylethyl, and cyclobutylmethyl.

Examples of the alkyl groups having 1-3 carbon atoms which are represented by $R^{2a}$ and $R^{3a}$ include methyl, ethyl, propyl, isopropyl, or cyclopropyl.

Examples of the alkyl group having 1-16 carbon atoms which is represented by $R^{5a}$ include methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, 1-ethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, cyclopropyl, cyclobutyl, cyclopentyl, cyclohexyl, cyclopropylmethyl, cyclopropylethyl, cyclobutylmethyl, heptyl, cyclohexylmethyl, 1,1-diethylpropyl, 2-methylcyclohexyl, 4-methylcyclohexyl, octyl, 1,1-diethyl-2-methylpropyl, 2,5-dimethylcyclohexyl, 3,5-dimethylcyclohexyl, 1,1,3,3-tetramethylbutyl, 1-methyl-1-propylbutyl, 1,1,2,3,3-pentamethylbutyl, 1,1-diethyl-3,3-dimethylbutyl, adamantyl, 1,1-dimethyloctyl, 1,1-dipropylbutyl, 1,1-dimethyldecyl, 1,1-diethyloctyl, 1,1-dibutylpentyl, 1,1-dibutylhexyl, 1,1-dibutylheptyl, or 1,1-dipentylhexyl.

These alkyl groups may have been substituted with fluorine atoms. Examples of such groups include trifluoromethyl, 2,2,2-trifluoroethyl, perfluoroethyl, perfluoropropyl, perfluoroisopropyl, perfluorobutyl, perfluoro-sec-butyl, perfluoro-tert-butyl, perfluorohexyl, perfluoroheptyl, perfluorooctyl, perfluorononyl, perfluorodecyl, perfluoroundecyl, perfluorododecyl, perfluorotridecyl, perfluorotetradecyl, perfluoropentadecyl, or perfluorohexadecyl.

Examples of the alkyl groups having 1-4 carbon atoms which are represented by $R^7$ and $R^8$ include methyl, ethyl, propyl, isopropyl, butyl, isobutyl, sec-butyl, and tert-butyl. These alkyl groups may have been substituted with fluorine atoms. Examples of such groups include trifluoromethyl, 2,2, 2-trifluoroethyl, perfluoroethyl, perfluoropropyl, perfluoroisopropyl, perfluorobutyl, perfluoro-sec-butyl, and perfluoro-tert-butyl.

It is preferred that $R^{1a}$ and $R^{4a}$ should be alkyl groups having 2-6 carbon atoms, among the groups shown above. More preferred are alkyl groups having 4 or 5 carbon atoms. Examples thereof include butyl, isobutyl, sec-butyl, tert-butyl, pentyl, isopentyl, neopentyl, tert-pentyl, 1-methylbutyl, 2-methylbutyl, 1,2-dimethylpropyl, or 1-ethylpropyl.

$R^{2a}$ and $R^{3a}$ preferably are hydrogen atoms.

It is preferred that $R^{5a}$ should be an alkyl group having 1-8 carbon atoms. For example, $R^{5a}$ preferably is methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, 1-ethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, cyclopropyl, cyclobutyl, cyclopentyl, cyclohexyl, cyclopropylmethyl, cyclopropylethyl, cyclobutylmethyl, heptyl, cyclohexylmethyl, 1,1-diethylpropyl, 2-methylcyclohexyl, 4-methylcyclohexyl, octyl, 1,1-diethyl-2-methylpropyl, 2,5-dimethylcyclohexyl, 3,5-dimethylcyclohexyl, 1,1,3,3-tetramethylbutyl, or 1-methyl-1-propylbutyl. It is more preferred that $R^{5a}$ should be an alkyl group having 3-5 carbon atoms. For example, $R^{5a}$ more preferably is propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, or 1-ethylpropyl.

$R^7$ and $R^8$ preferably are methyl or ethyl, and more preferably are methyl.

The amide complex (4) to be used as a starting material can be synthesized with reference to a known method (patent document 1).

The organic solvent to be used in production process 2 may be any organic solvent which reacts with neither the amide complex (4) nor the alcohol (5). Examples thereof include alkanes such as pentane, hexane, heptane, octane, cyclohexane, methylcyclohexane, and ethylcyclohexane, aromatic hydrocarbons such as benzene, toluene, and xylene, and ethers such as diethyl ether, diisopropyl ether, dibutyl ether, tetrahydrofuran, dioxane, ethylene glycol dimethyl ether, diglyme, triglyme, and cyclopentyl methyl ether. These may be used alone or as a mixture thereof.

From the standpoint of obtaining the titanium complex (1a) by production process 2 in satisfactory yield, it is preferred that the alcohol (5) should be added to a solution prepared beforehand by dissolving the amide complex (4) in an organic solvent.

It is preferred in production process 2 that the alcohol (5) should be subjected to reaction in an amount of 1.6-2.4 equivalents to the amide complex (4) from the standpoint of obtaining the titanium complex (1a) in satisfactory yield. It is more preferred to cause the alcohol (5) to act in an amount of 2.0 equivalents to the amide complex (4).

The titanium complex (1a) obtained by production process 2 can be isolated by using suitably selected general techniques for purification of complexes, such as distillation, sublimation, and crystallization.

A titanium-containing thin film can be produced using the titanium complex (1) of the invention as a material. Examples of thin films which can be produced include thin films of titanium oxide, titanium nitride, titanium carbide, and the like and thin films of composite metal compounds containing titanium and other metal(s), such as strontium titanate and barium titanate. The titanium complex (1) is suitable for use as a material for producing thin films of either titanium oxide or a composite oxide since oxygen atoms are contained in the molecule thereof. Methods for forming a titanium-containing thin film are not particularly limited, and examples thereof include the CVD method, ALD method, ink-jet method, spin coating, dip coating, or solution method. In the case where a thin film is produced by the CVD method or the ALD method, the titanium complex (1) is vaporized and fed as a gas to a reaction chamber. Examples of methods for vaporizing the titanium complex (1) include a bubbling method and a liquid injection method. The bubbling method is a method in which carrier gas, such as helium, neon, argon, krypton, xenon, nitrogen, or the like is bubbled into the titanium complex (1) held in a container heated at a given temperature and the titanium complex (1) is thereby vaporized. The liquid injection method is a method in which the titanium complex (1) in a liquid state is fed to a vaporizer and heated in the vaporizer to thereby vaporize the titanium complex (1). In the liquid injection method, the titanium complex (1) may be dissolved in a solvent and used as the solution. Examples of the solvent to be used when the titanium complex (1) is used as a solution include ethers such as 1,2-dimethoxyethane, diglyme, triglyme, dioxane, tetrahydrofuran, and cyclopentyl methyl ether, alkanes such as hexane, cyclohexane, methylcyclohexane, ethylcyclohexane, heptane, octane, nonane, and decane, and aromatic hydrocarbons such as benzene, toluene, ethylbenzene, and xylene. These solvents may be used alone or as a mixture thereof.

By decomposing the titanium complex (1) fed as a gas to the reaction chamber, a titanium-containing thin film can be formed on a substrate. Examples of methods for decomposing the titanium complex (1) include a thermal method, a method in which a plasma, light, or the like is used, and a method in which a reactant gas such as water, oxygen, ozone, hydrogen peroxide, hydrogen, or ammonia is fed to the inside of the reaction chamber and caused to induce a chemical reaction. By using these methods either alone or in combination, the titanium complex (1) can be decomposed to form a titanium-containing thin film.

The titanium-containing thin film of the invention can be used as a constituent element of a semiconductor device, such as a DRAM, SRAM, FeRAM, ReRAM, MRAM, PRAM, or flash memory, or as a photocatalyst.

EXAMPLES

The invention will be explained below in more detail by reference to Examples. However, the invention should not be construed as being limited to the Examples.

Example 1

In an argon atmosphere, 1.38 g (9.83 mmol) of N,N'-diisopropyl-1,4-diaza-1,3-butadiene ($^i$PrNCHCHN$^i$Pr) was dissolved in a liquid mixture of 12 mL of hexane and 2 mL of tetrahydrofuran, and 143 mg (20.6 mmol) of lithium was added thereto. The resultant mixture was stirred in that atmosphere at room temperature for 12 hours. A solution prepared by dissolving 3.90 g (9.83 mmol) of tetrakis(tert-pentyloxo) titanium (Ti(O$^t$Pe)$_4$) in 10 mL of hexane was added to the liquid reaction mixture, and the resultant mixture was stirred at room temperature for 14 hours. To this liquid reaction mixture was further added 2.14 g (19.7 mmol) of chlorotrimethylsilane. This mixture was stirred at room temperature for 6 hours. The insoluble matter generated was taken out by filtration, and the solvent was removed from the filtrate by distillation at a reduced pressure. The resultant residue was subjected to vacuum distillation (distillation temperature 95° C./0.07 Torr) to thereby obtain ethene-1,2-diylbis(isopropylamido)bis(tert-pentyloxo)titanium (Ti($^i$PrNCHCHN$^i$Pr)(O$^t$Pe)$_2$) as a deep-red liquid (amount obtained, 3.29 g; yield, 92%).

$^1$H NMR (500 MHz, C$_6$D$_6$, δ/ppm) 5.78 (s, 2H), 3.55 (sept, J=6 Hz, 2H), 1.59 (q, J=8 Hz, 4H), 1.33 (s, 12H), 1.25 (br, 12H), 1.04 (t, J=8 Hz, 6H)

$^{13}$C NMR (125 MHz, C$_6$D$_6$, δ/ppm) 106.0, 82.8, 81.6 (br), 56.8, 38.2, 37.8, 26.1, 9.55, 9.48.

Test Example 1

Thermal Analyses of Ti($^i$PrNCHCHN$^i$Pr)(O$^t$Pe)$_2$

In FIG. 1 are shown the results of TG (thermogravimetry) analysis of the Ti($^i$PrNCHCHN$^i$Pr)(O$^t$Pe)$_2$, in which a measurement was made under the conditions of a heating rate of 10° C./min in an atmosphere through which argon was continuously passed at 400 mL/min, and the results of DSC (differential scanning calorimetry) analysis of the Ti($^i$PrNCHCHN$^i$Pr)(O$^t$Pe)$_2$, in which a measurement was made in a sealed container at a heating rate of 10° C./min. It is apparent from the results of TG that the Ti($^i$PrNCHCHN$^i$Pr)(O$^t$Pe)$_2$ has vaporization characteristics that make this complex suitable for use as a material in the CVD method, ALD method, or the like. It is apparent from the results of DSC that the Ti($^i$PrNCHCHN$^i$Pr)(O$^t$Pe)$_2$ has satisfactory thermal stability.

Example 2

In an argon atmosphere, 2.01 g (6.62 mmol) of ethene-1,2-diylbis(tert-butylamido)bis(dimethylamido)titanium (Ti($^t$BuNCHCHN$^t$Bu)(NMe$_2$)$_2$) was dissolved in 8 mL of hexane, and 610 mg (13.2 mmol) of ethanol was added thereto. The resultant mixture was stirred in that atmosphere at room temperature for 12 hours. The solvent was removed from this liquid reaction mixture by distillation at a reduced pressure, and the resultant residue was subjected to vacuum distillation (distillation temperature 85° C./0.05 Torr) to thereby obtain ethene-1,2-diylbis(tert-butylamido)diethoxotitanium (Ti($^t$BuNCHCHN$^t$Bu)(OEt)$_2$) as a deep-red liquid (amount obtained, 1.88 g; yield, 93%).

$^1$H NMR (500 MHz, C$_6$D$_6$, δ/ppm) 5.98 (s, 2H), 4.20 (br, 4H), 1.29 (s, 18H), 1.16-1.32 (br, 6H)

$^{13}$C NMR (125 MHz, C$_6$D$_6$, δ/ppm) 102.4, 68-70 (br), 58.0, 31.6, 21.2.

Test Example 2

Thermal Analyses of Ti($^t$BuNCHCHN$^t$Bu)(OEt)$_2$

Figure 2:
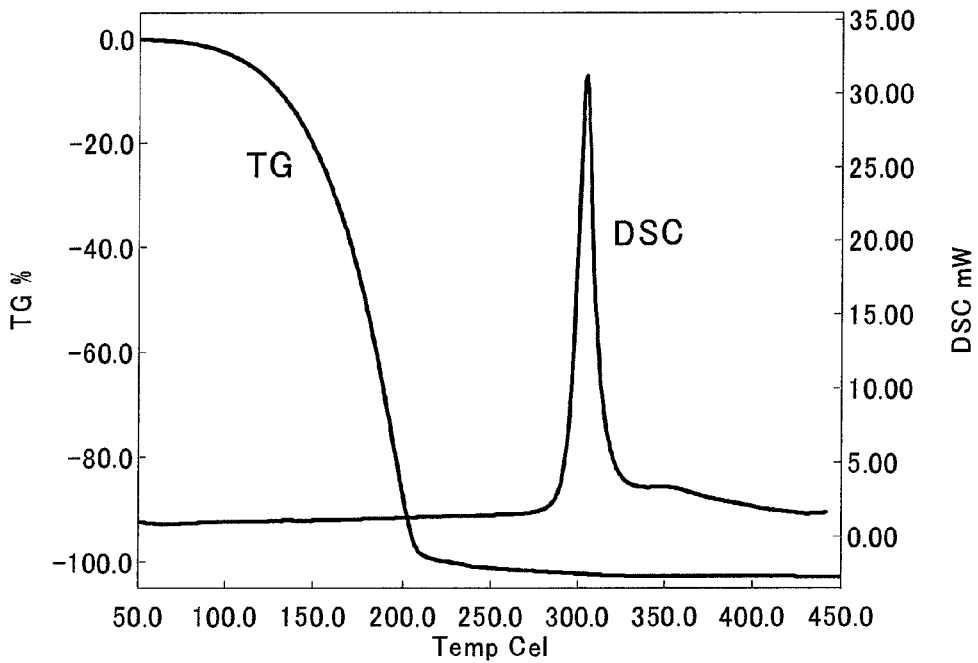
FIG. 2 is a presentation showing the results of the TG and DSC analyses conducted in Test Example 2.

In FIG. 2 are shown the results of TG analysis of the Ti($^t$BuNCHCHN$^t$Bu)(OEt)$_2$, in which a measurement was made under the conditions of a heating rate of 10° C./min in an atmosphere through which argon was continuously passed at 400 mL/min, and the results of DSC analysis of the Ti($^t$BuNCHCHN$^t$Bu)(OEt)$_2$, in which a measurement was made in a sealed container at a heating rate of 10° C./min. It is apparent from the results of TG that the Ti($^t$BuNCHCHN$^t$Bu)(OEt)$_2$ has vaporization characteristics that make this complex suitable for use as a material in the CVD method, ALD method, or the like. It is apparent from the results of DSC that the Ti($^t$BuNCHCHN$^t$Bu)(OEt)$_2$ has satisfactory thermal stability.

Example 3

In an argon atmosphere, 2.22 g (13.2 mmol) of N,N'-di(tert-butyl)-1,4-diaza-1,3-butadiene ($^t$BuNCHCHN$^t$Bu) was dissolved in 20 mL of tetrahydrofuran, and 606 mg (26.4 mmol) of sodium was added thereto. The resultant mixture was stirred in that atmosphere at room temperature for 12 hours. A solution prepared by dissolving 3.56 g (12.5 mmol) of tetraisopropoxotitanium (Ti(O$^i$Pr)$_4$) in 10 mL of hexane was added to the liquid reaction mixture, and the resultant mixture was stirred at room temperature for 12 hours. The solvent was removed from this liquid reaction mixture by distillation at a reduced pressure, and 20 mL of hexane was added to the residue. The insoluble matter generated was taken out by filtration, and the solvent was removed from the filtrate by distillation at a reduced pressure. The resultant residue was subjected to vacuum distillation (distillation temperature 85° C./0.05 Torr) to thereby obtain ethene-1,2-diylbis(tert-butylamido)diisopropoxotitanium (Ti($^t$BuNCHCHN$^t$Bu)(O$^i$Pr)$_2$) as a deep-red liquid (amount obtained, 3.91 g; yield, 93%).

$^1$H NMR (500 MHz, C$_6$D$_6$, δ/ppm) 5.96 (s, 2H), 4.0-5.0 (br, 2H), 1.30 (s, 18H), 1.1-1.3 (br, 12H)

$^{13}$C NMR (125 MHz, C$_6$D$_6$, δ/ppm) 102.7, 74.5 (br), 57.6, 31.7, 27.8.

Test Example 3

Thermal Analyses of Ti($^t$BuNCHCHN$^t$Bu)(O$^i$Pr)$_2$

Figure 3:
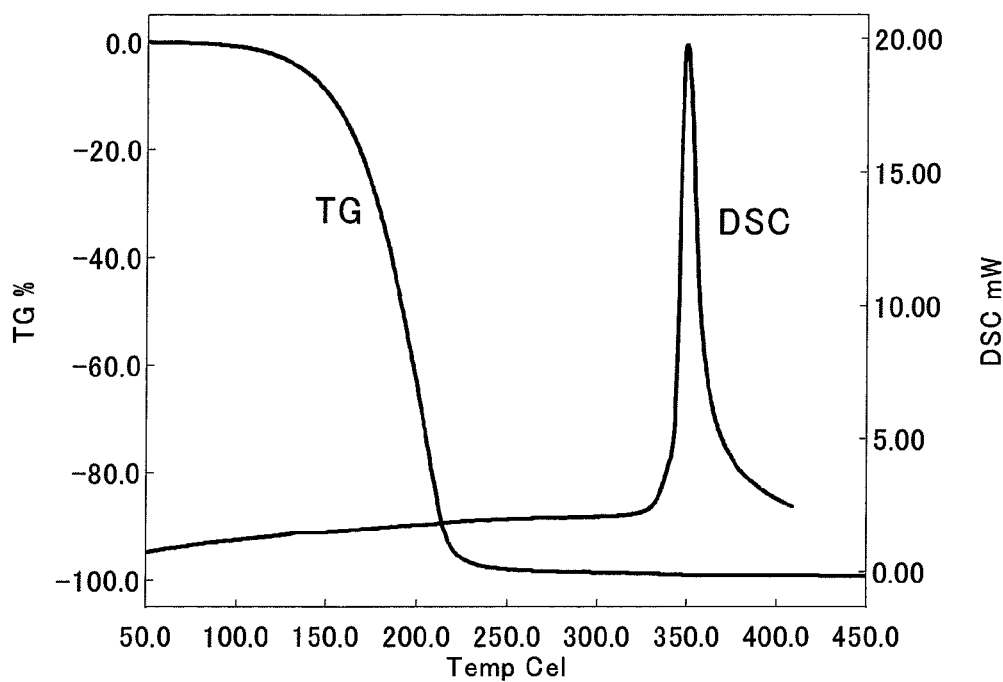
FIG. 3 is a presentation showing the results of the TG and DSC analyses conducted in Test Example 3.

In FIG. 3 are shown the results of TG analysis of the Ti($^t$BuNCHCHN$^t$Bu)(O$^i$Pr)$_2$, in which a measurement was made under the conditions of a heating rate of 10° C./min in an atmosphere through which argon was continuously passed at 400 mL/min, and the results of DSC analysis of the Ti($^t$BuNCHCHN$^t$Bu)(O$^i$Pr)$_2$, in which a measurement was made in a sealed container at a heating rate of 10° C./min. It is apparent from the results of TG that the Ti($^t$BuNCHCHN$^t$Bu)(O$^i$Pr)$_2$ has vaporization characteristics that make this complex suitable for use as a material in the CVD method, ALD method, or the like. It is apparent from the results of DSC that the Ti($^t$BuNCHCHN$^t$Bu)(O$^i$Pr)$_2$ has satisfactory thermal stability.

Example 4

In an argon atmosphere, 6.01 g (19.7 mmol) of ethene-1,2-diylbis(tert-butylamido)bis(dimethylamido)titanium (Ti($^t$BuNCHCHN$^t$Bu)(NMe$_2$)$_2$) was dissolved in 20 mL of toluene, and 2.37 g (39.4 mmol) of 2-propanol was added thereto. The resultant mixture was stirred in that atmosphere at room temperature for 2 hours. The solvent was removed from this liquid reaction mixture by distillation at a reduced pressure, and the resultant residue was subjected to vacuum distillation (distillation temperature 85° C./0.05 Torr) to thereby obtain Ti($^t$BuNCHCHN$^t$Bu)(O$^i$Pr)$_2$ as a deep-red liquid (amount obtained, 6.21 g; yield, 94%). The Ti($^t$BuNCHCHN$^t$Bu)(O$^i$Pr)$_2$ thus obtained was examined for $^1$H and $^{13}$C NMR spectra. As a result, these spectra agreed with the spectra of the product obtained in Example 3.

Example 5

In an argon atmosphere, 1.76 g (5.78 mmol) of Ti($^t$BuNCHCHN$^t$Bu)(NMe$_2$)$_2$ was dissolved in 7 mL of hexane, and 1.02 g (11.6 mmol) of tert-pentyl alcohol was added thereto. The resultant mixture was stirred in that atmosphere at room temperature for 12 hours. The solvent was removed from this liquid reaction mixture by distillation at a reduced pressure, and the resultant residue was subjected to vacuum distillation (distillation temperature 97° C./0.05 Torr) to thereby obtain ethene-1,2-diylbis(tert-butylamido)bis(tert-pentyloxo)titanium (Ti($^t$BuNCHCHN$^t$Bu)(O$^t$Pe)$_2$) as a deep-red liquid (amount obtained, 2.11 g; yield, 93%).

$^1$H NMR (500 MHz, C$_6$D$_6$, δ/ppm) 5.93 (s, 2H), 1.55 (br, 4H), 1.30 (s, 18H), 1.1-1.4 (br, 12H), 0.99 (br, 6H)

$^{13}$C NMR (125 MHz, C$_6$D$_6$, δ/ppm) 103.1, 81.4 (br), 57.4, 38.3, 31.9, 31.1, 9.8.

Test Example 4

Thermal Analyses of Ti($^t$BuNCHCHN$^t$Bu)(O$^t$Pe)$_2$

Figure 4:
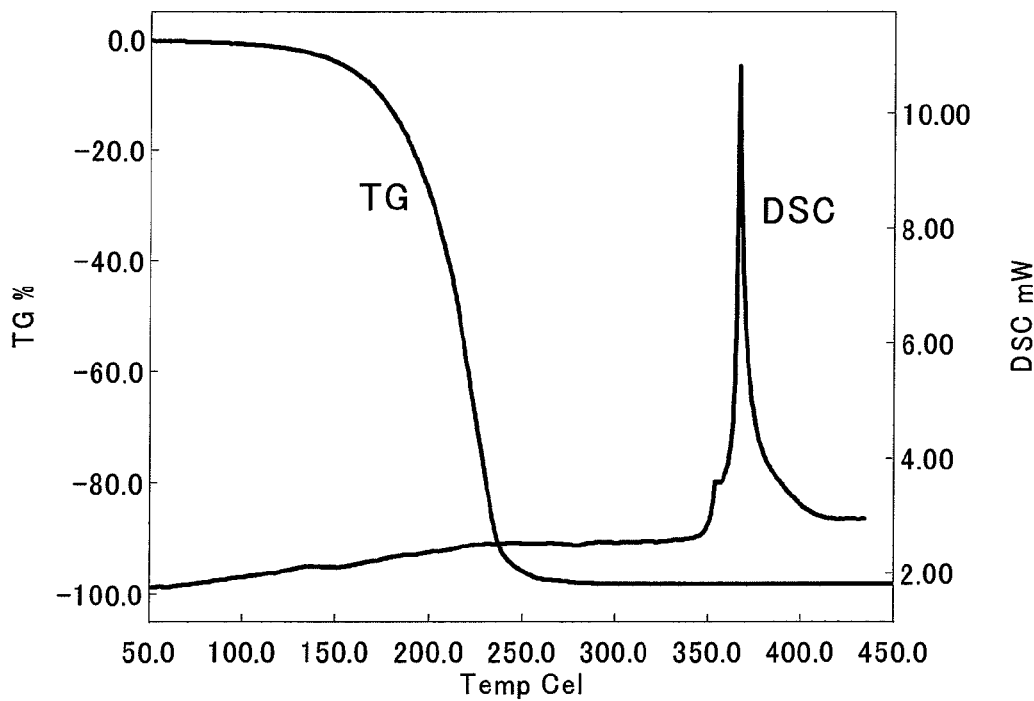
FIG. 4 is a presentation showing the results of the TG and DSC analyses conducted in Test Example 4.

In FIG. 4 are shown the results of TG analysis of the Ti($^t$BuNCHCHN$^t$Bu)(O$^t$Pe)$_2$, in which a measurement was made under the conditions of a heating rate of 10° C./min in an atmosphere through which argon was continuously passed at 400 mL/min, and the results of DSC analysis of the Ti($^t$BuNCHCHN$^t$Bu)(O$^t$Pe)$_2$, in which a measurement was made in a sealed container at a heating rate of 10° C./min. It is apparent from the results of TG that the Ti($^t$BuNCHCHN$^t$Bu)(O$^t$Pe)$_2$ has vaporization characteristics that make this complex suitable for use as a material in the CVD method, ALD method, or the like. It is apparent from the results of DSC that the Ti($^t$BuNCHCHN$^t$Bu)(O$^t$Pe)$_2$ has satisfactory thermal stability.

Example 6

In an argon atmosphere, 2.61 g (8.58 mmol) of Ti($^t$BuNCHCHN$^t$Bu)(NMe$_2$)$_2$ was dissolved in 10 mL of hexane, and 2.00 g (17.2 mmol) of 3-ethyl-3-pentanol was added thereto. The resultant mixture was stirred in that atmosphere at room temperature for 14 hours. The solvent was removed from this liquid reaction mixture by distillation at a reduced pressure, and the resultant residue was subjected to vacuum distillation (distillation temperature 112° C./0.03 Torr) to thereby obtain ethene-1,2-diylbis(tert-butylamido)bis(1,1-diethylpropyloxo)titanium (Ti($^t$BuNCHCHN$^t$Bu)(OCEt$_3$)$_2$) as a deep-red liquid (amount obtained, 1.93 g; yield, 50%).

$^1$H NMR (500 MHz, C$_6$D$_6$, δ/ppm) 5.95 (s, 2H), 1.55 (br, 12H), 1.33 (s, 18H), 0.96 (br, 18H)

$^{13}$C NMR (125 MHz, C$_6$D$_6$, δ/ppm) 103.0, 86.0 (br), 57.5, 32.3, 31.5, 8.8.

Test Example 5

Thermal Analyses of Ti($^t$BuNCHCHN$^t$Bu)(OCEt$_3$)$_2$

Figure 5:
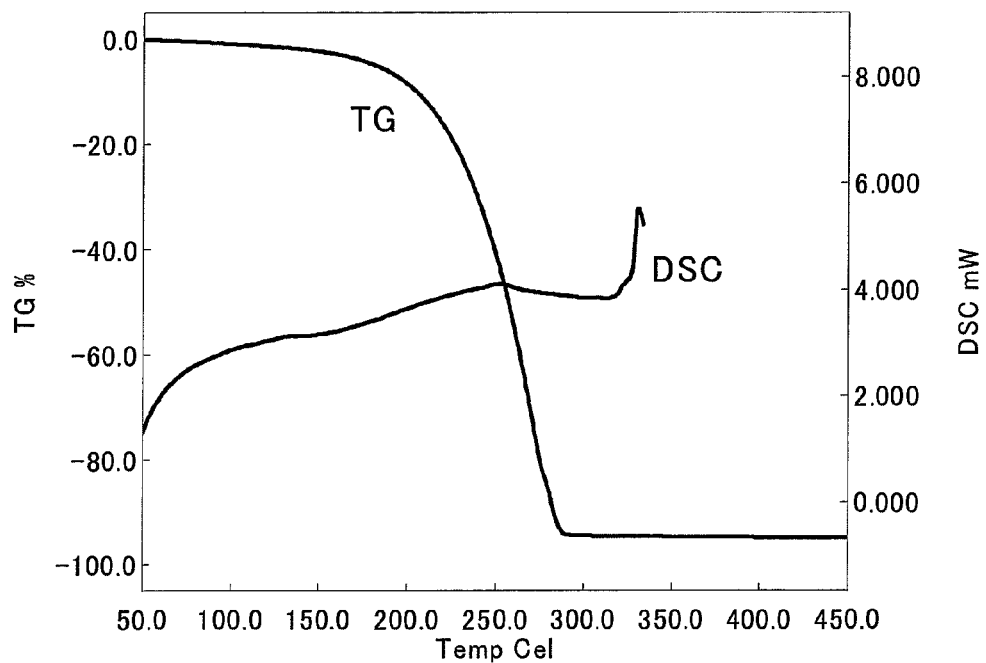
FIG. 5 is a presentation showing the results of the TG and DSC analyses conducted in Test Example 5.

In FIG. 5 are shown the results of TG analysis of the Ti($^t$BuNCHCHN$^t$Bu)(OCEt$_3$)$_2$, in which a measurement was made under the conditions of a heating rate of 10° C./min in an atmosphere through which argon was continuously passed at 400 mL/min, and the results of DSC analysis of the Ti($^t$BuNCHCHN$^t$Bu)(OCEt$_3$)$_2$, in which a measurement was made in a sealed container at a heating rate of 10° C./min. It is apparent from the results of TG that the Ti($^t$BuNCHCHN$^t$Bu)(OCEt$_3$)$_2$ has vaporization characteristics that make this complex suitable for use as a material in the CVD method, ALD method, or the like. It is apparent from the results of DSC that the Ti($^t$BuNCHCHN$^t$Bu)(OCEt$_3$)$_2$ has satisfactory thermal stability.

Example 7

In an argon atmosphere, 3.09 g (10.2 mmol) of Ti($^t$BuNCHCHN$^t$Bu)(NMe$_2$)$_2$ was dissolved in 10 mL of hexane, and 2.64 g (20.3 mmol) of 1,1-diethyl-2-methylpropyl alcohol was added thereto. The resultant mixture was stirred in that atmosphere at room temperature for 4.5 hours. The solvent was removed from this liquid reaction mixture by distillation at a reduced pressure, and the resultant residue was subjected to vacuum distillation (oil bath temperature 190° C./0.06 Torr) to thereby obtain ethene-1,2-diylbis(tert-butylamido)bis(1,1-diethyl-2-methylpropyloxo)titanium (Ti($^t$BuNCHCHN$^t$Bu)(OCEt$_2$CHMe$_2$)$_2$) as a deep-red solid (amount obtained, 3.35 g; yield, 69%).

1H NMR (500 MHz, C$_6$D$_6$, δ/ppm) 5.97 (s, 2H), 1.61 (br, 10H), 1.34 (s, 18H), 1.00 (br, 24H)

$^{13}$C NMR (125 MHz, C$_6$D$_6$, δ/ppm) 103.2, 88.1 (br), 57.9, 34.8, 31.5, 29.5, 17.8, 8.7.

Test Example 6

Thermal Analyses of Ti($^t$BuNCHCHN$^t$Bu)(OCEt$_2$CHMe$_2$)$_2$

Figure 6:
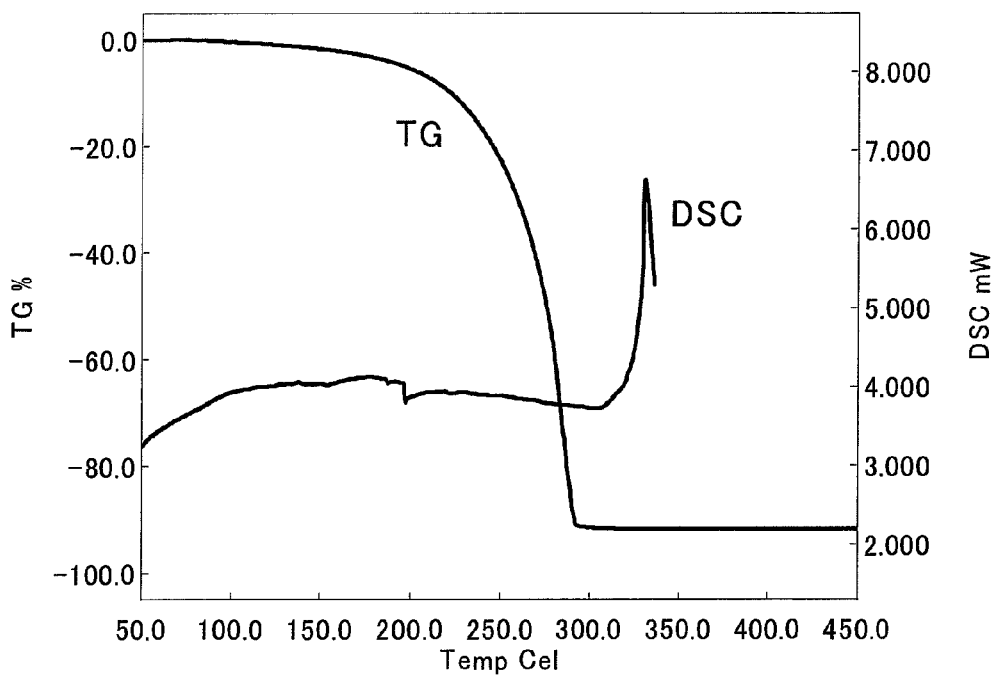
FIG. 6 is a presentation showing the results of the TG and DSC analyses conducted in Test Example 6.

In FIG. 6 are shown the results of TG analysis of the Ti($^t$BuNCHCHN$^t$Bu)(OCEt$_2$CHMe$_2$)$_2$, in which a measurement was made under the conditions of a heating rate of 10° C./min in an atmosphere through which argon was continuously passed at 400 mL/min, and the results of DSC analysis of the Ti($^t$BuNCHCHN$^t$Bu)(OCEt$_2$CHMe$_2$)$_2$, in which a measurement was made in a sealed container at a heating rate of 10° C./min. It is apparent from the results of TG that the Ti($^t$BuNCHCHN$^t$Bu)(OCEt$_2$CHMe$_2$)$_2$ has vaporization characteristics that make this complex suitable for use as a material in the CVD method, ALD method, or the like. It is apparent from the results of DSC that the Ti($^t$BuNCHCHN$^t$Bu)(OCEt$_2$CHMe$_2$)$_2$ has satisfactory thermal stability.

Example 8

In an argon atmosphere, 4.11 g (13.5 mmol) of Ti($^t$BuNCHCHN$^t$Bu)(NMe$_2$)$_2$ was dissolved in 20 mL of hexane, and 2.70 g (27.0 mmol) of 2,2,2-trifluoroethanol was added thereto. The resultant mixture was stirred in that atmosphere at room temperature for 12 hours. The solvent was removed from this liquid reaction mixture by distillation at a reduced pressure, and the resultant residue was subjected to vacuum distillation (distillation temperature 90° C./0.10 Torr) to thereby obtain ethene-1,2-diylbis(tert-butylamido)bis(2,2,2-trifluoroethoxo)titanium (Ti($^t$BuNCHCHN$^t$Bu)(OCH$_2$CF$_3$)$_2$) as a deep-red liquid (amount obtained, 4.94 g; yield, 88%).

$^1$H NMR (500 MHz, C$_6$D$_6$, δ/ppm) 5.90 (s, 2H), 4.4 (br, 2H), 3.8 (br, 2H), 1.14 (s, 18H)

$^{13}$C NMR (125 MHz, C$_6$D$_6$, δ/ppm) 125.3 (q, J=279 Hz), 101.4, 70-72 (br), 68-70 (br), 59.7, 31.0

$^{19}$F NMR (470 MHz, C$_6$D$_6$, δ/ppm) −78.5 (br), −79.2 (br).

Test Example 7

Thermal Analyses of Ti($^t$BuNCHCHN$^t$Bu)(OCH$_2$CF$_3$)$_2$

Figure 7:
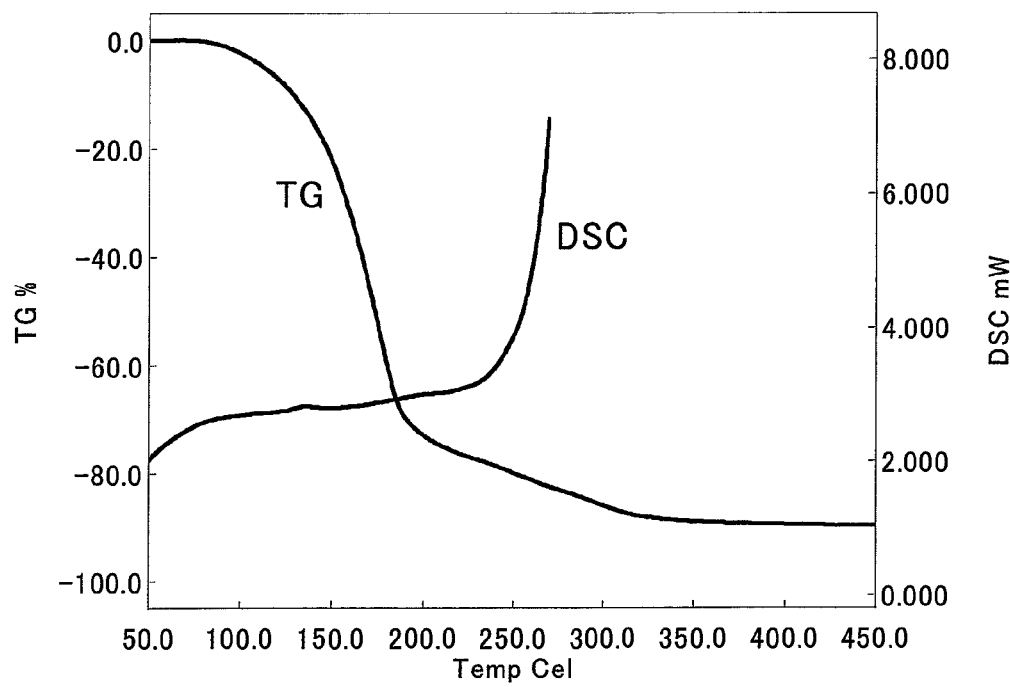
FIG. 7 is a presentation showing the results of the TG and DSC analyses conducted in Test Example 7.

In FIG. 7 are shown the results of TG analysis of the Ti($^t$BuNCHCHN$^t$Bu)(OCH$_2$CF$_3$)$_2$, in which a measurement was made under the conditions of a heating rate of 10° C./min in an atmosphere through which argon was continuously passed at 400 mL/min, and the results of DSC analysis of the Ti($^t$BuNCHCHN$^t$Bu)(OCH$_2$CF$_3$)$_2$, in which a measurement was made in a sealed container at a heating rate of 10° C./min. It is apparent from the results of TG that the Ti($^t$BuNCHCHN$^t$Bu)(OCH$_2$CF$_3$)$_2$ has vaporization characteristics that make this complex suitable for use as a material in the CVD method, ALD method, or the like. It is apparent from the results of DSC that the Ti($^t$BuNCHCHN$^t$Bu)(OCH$_2$CF$_3$)$_2$ has satisfactory thermal stability.

Reference Example 1

In an argon atmosphere, 379 mg (54.6 mmol) of lithium was added to a solution prepared by dissolving 5.31 g (27.0 mmol) of N,N'-di(tert-pentyl)-1,4-diaza-1,3-butadiene ($^t$PeNCHCHN$^t$Pe) in 50 mL of tetrahydrofuran, and the resultant mixture was stirred at room temperature for 14 hours. The residual lithium was taken out by filtration, and the solvent was removed from the filtrate by distillation at a reduced pressure. The residual yellow solid was suspended in 30 mL of hexane, and a solution prepared by dissolving 5.77 g (25.7 mmol) of tetrakis(dimethylamido)titanium (Ti(NMe$_2$)$_4$) in 10 mL of hexane was added thereto. The resultant mixture was stirred at 50° C. for 4 hours and then cooled to room temperature, and the insoluble matter was taken out by filtration. The solvent was removed from the filtrate by distillation at a reduced pressure, and the resultant residue was subjected to vacuum distillation to thereby obtain ethene-1,2-diylbis(tert-pentylamido)bis(dimethylamido)titanium (Ti($^t$PeNCHCHN$^t$Pe)(NMe$_2$)$_2$) as a deep-red liquid (amount obtained, 7.83 g; yield, 91%).

$^1$H NMR (500 MHz, C$_6$D$_6$, δ/ppm) 5.77 (s, 2H), 3.04 (br, 6H), 1.51 (q, J=8 Hz, 4H), 1.24 (s, 12H), 0.77 (t, J=8 Hz, 6H)
$^{13}$C NMR (125 MHz, C$_6$D$_6$, δ/ppm) 101.6, 60.9, 43.4, 36.4, 28.5, 8.9.

Example 9

In an argon atmosphere, 3.43 g (10.3 mmol) of Ti($^t$PeNCHCHN$^t$Pe)(NMe$_2$)$_2$ was dissolved in 15 mL of hexane, and 661 mg (20.6 mmol) of methanol was added thereto. The resultant mixture was stirred in that atmosphere at room temperature for 14 hours. The solvent was removed from this liquid reaction mixture by distillation at a reduced pressure, and the resultant residue was subjected to vacuum distillation (distillation temperature 106° C./0.10 Torr) to thereby obtain ethene-1,2-diylbis(tert-pentylamido)dimethoxotitanium (Ti($^t$PeNCHCHN$^t$Pe)(OMe)$_2$) as a deep-red viscous liquid (amount obtained, 2.92 g; yield, 92%).

$^1$H NMR (500 MHz, C$_6$D$_6$, δ/ppm) 6.02 (s, 2H), 3.99 (br, 6H), 1.54 (q, J=8 Hz, 4H), 1.27 (s, 12H), 0.78 (t, J=8 Hz, 6H)
$^{13}$C NMR (125 MHz, C$_6$D$_6$, δ/ppm) 103.0, 61.4, 61.2 (br), 37.0, 28.5, 9.3.

Test Example 8

Thermal Analyses of Ti($^t$PeNCHCHN$^t$Pe)(OMe)$_2$

Figure 8:
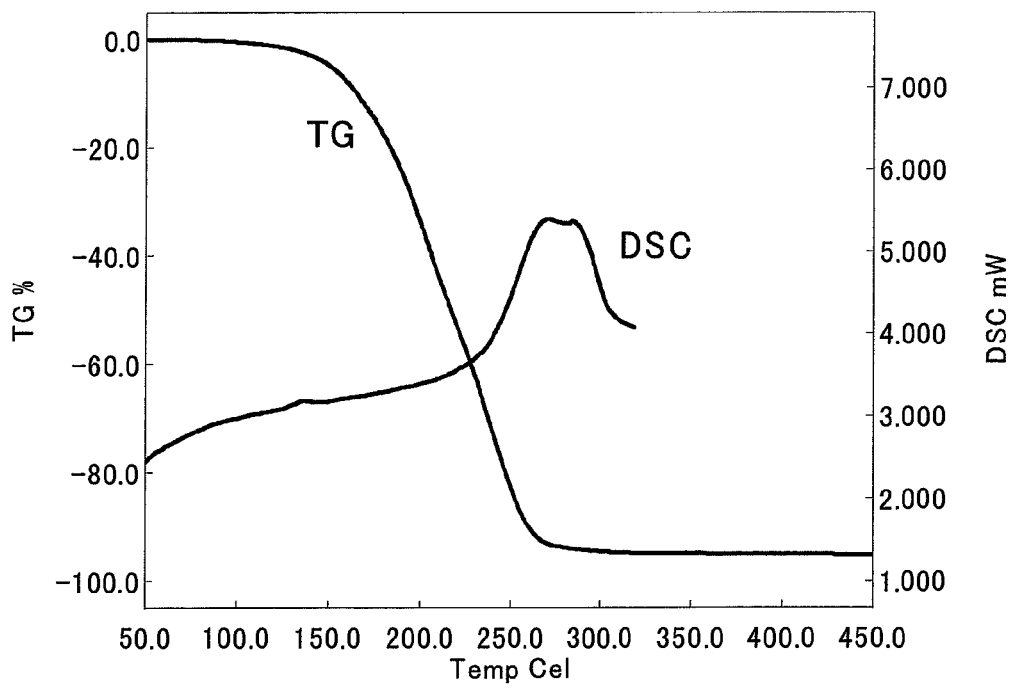
FIG. 8 is a presentation showing the results of the TG and DSC analyses conducted in Test Example 8.

In FIG. 8 are shown the results of TG analysis of the Ti($^t$PeNCHCHN$^t$Pe)(OMe)$_2$, in which a measurement was made under the conditions of a heating rate of 10° C./min in an atmosphere through which argon was continuously passed at 400 mL/min, and the results of DSC analysis of the Ti($^t$PeNCHCHN$^t$Pe)(OMe)$_2$, in which a measurement was made in a sealed container at a heating rate of 10° C./min. It is apparent from the results of TG that the Ti($^t$PeNCHCHN$^t$Pe)(OMe)$_2$ has vaporization characteristics that make this complex suitable for use as a material in the CVD method, ALD method, or the like. It is apparent from the results of DSC that the Ti($^t$PeNCHCHN$^t$Pe)(OMe)$_2$ has satisfactory thermal stability.

Example 10

In an argon atmosphere, 2.21 g (6.65 mmol) of Ti($^t$PeNCHCHN$^t$Pe)(NMe$_2$)$_2$ was dissolved in 10 mL of hexane, and 613 mg (13.3 mmol) of ethanol was added thereto. The resultant mixture was stirred in that atmosphere at room temperature for 8 hours. The solvent was removed from this liquid reaction mixture by distillation at a reduced pressure, and the resultant residue was subjected to vacuum distillation (distillation temperature 100° C./0.05 Torr) to thereby obtain ethene-1,2-diylbis(tert-pentylamido)diethoxotitanium (Ti($^t$PeNCHCHN$^t$Pe)(OEt)$_2$) as a deep-red liquid (amount obtained, 2.16 g; yield, 97%).

$^1$H NMR (500 MHz, C$_6$D$_6$, δ/ppm) 5.91 (s, 2H), 3.4-4.8 (br, 4H), 1.55 (q, J=8 Hz, 4H), 1.25 (12H), 1.1-1.5 (br, 6H), 0.80 (t, J=8 Hz, 6H)
$^{13}$C NMR (125 MHz, C$_6$D$_6$, δ/ppm) 102.3, 71.0 (br), 60.7, 36.6, 29.1 (br), 21.1, 9.2.

Test Example 9

Thermal Analyses of Ti($^t$PeNCHCHN$^t$Pe)(OEt)$_2$

Figure 9:
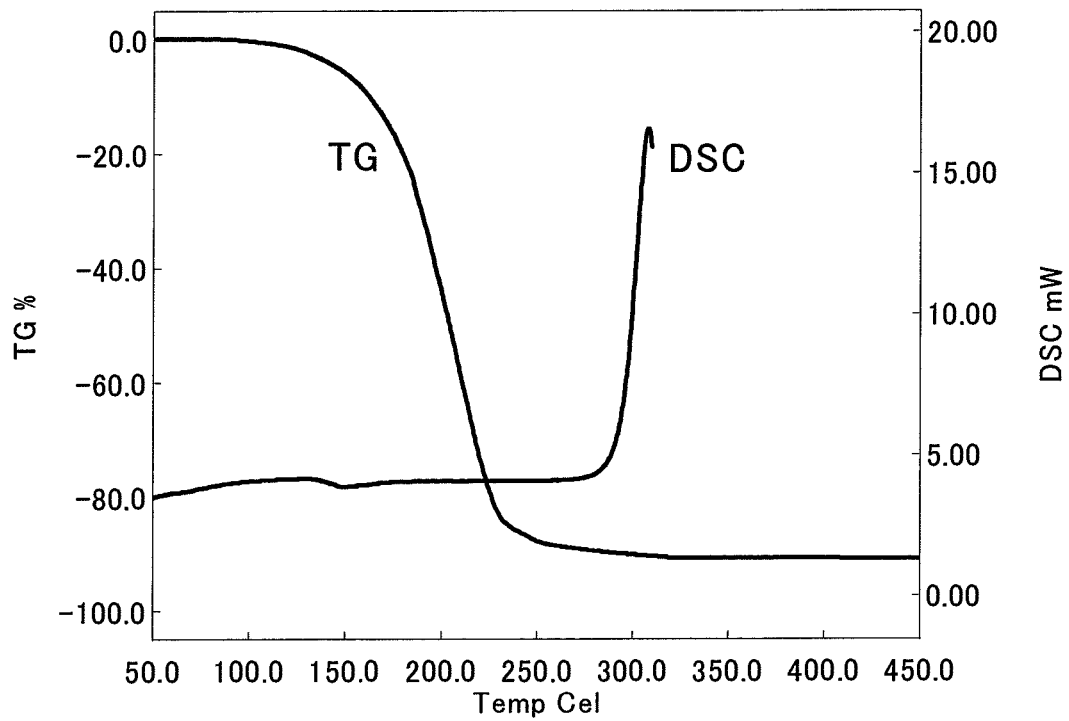
FIG. 9 is a presentation showing the results of the TG and DSC analyses conducted in Test Example 9.

In FIG. 9 are shown the results of TG analysis of the Ti($^t$PeNCHCHN$^t$Pe)(OEt)$_2$, in which a measurement was made under the conditions of a heating rate of 10° C./min in an atmosphere through which argon was continuously passed at 400 mL/min, and the results of DSC analysis of the Ti($^t$PeNCHCHN$^t$Pe)(OEt)$_2$, in which a measurement was made in a sealed container at a heating rate of 10° C./min. It is apparent from the results of TG that the Ti($^t$PeNCHCHN$^t$Pe)(OEt)$_2$ has vaporization characteristics that make this complex suitable for use as a material in the CVD method, ALD method, or the like. It is apparent from the results of DSC that the Ti($^t$PeNCHCHN$^t$Pe)(OEt)$_2$ has satisfactory thermal stability.

Example 11

In an argon atmosphere, 3.09 g (15.7 mmol) of N,N'-di(tert-pentyl)-1,4-diaza-1,3-butadiene ($^t$PeNCHCHN$^t$Pe) was dissolved in 30 mL of tetrahydrofuran, and 758 mg (33.0 mmol) of sodium was added thereto. The resultant mixture was stirred in that atmosphere at room temperature for 12 hours. A solution prepared by dissolving 4.25 g (15.0 mmol) of tetraisopropoxotitanium (Ti(O$^i$Pr)$_4$) in 10 mL of hexane was added to the liquid reaction mixture, and the resultant mixture was stirred at room temperature for 12 hours. The solvent was removed from this liquid reaction mixture by distillation at a reduced pressure, and 30 mL of hexane was added to the residue. The insoluble matter generated was taken out by filtration, and the solvent was removed from the filtrate by distillation at a reduced pressure. The resultant residue was subjected to vacuum distillation (distillation temperature 92° C./0.05 Torr) to thereby obtain ethene-1,2-diylbis(tert-pentylamido)diisopropoxotitanium (Ti($^t$PeNCHCHN$^t$Pe)(O$^i$Pr)$_2$) as a deep-red liquid (amount obtained, 4.96 g; yield, 92%).

$^1$H NMR (500 MHz, C$_6$D$_6$, δ/ppm) 5.90 (s, 2H), 3.7-5.2 (br, 2H), 1.56 (q, J=8 Hz, 4H), 1.26 (s, 12H), 0.9-1.6 (br, 12H), 0.81 (t, J=8 Hz, 6H)

$^{13}$C NMR (125 MHz, C$_6$D$_6$, δ/ppm) 102.6, 74.4 (br), 60.3, 36.8, 29.2 (br), 27.8, 9.3.

Test Example 10

Thermal Analyses of Ti($^t$PeNCHCHN$^t$Pe)(O$^i$Pr)$_2$

Figure 10:
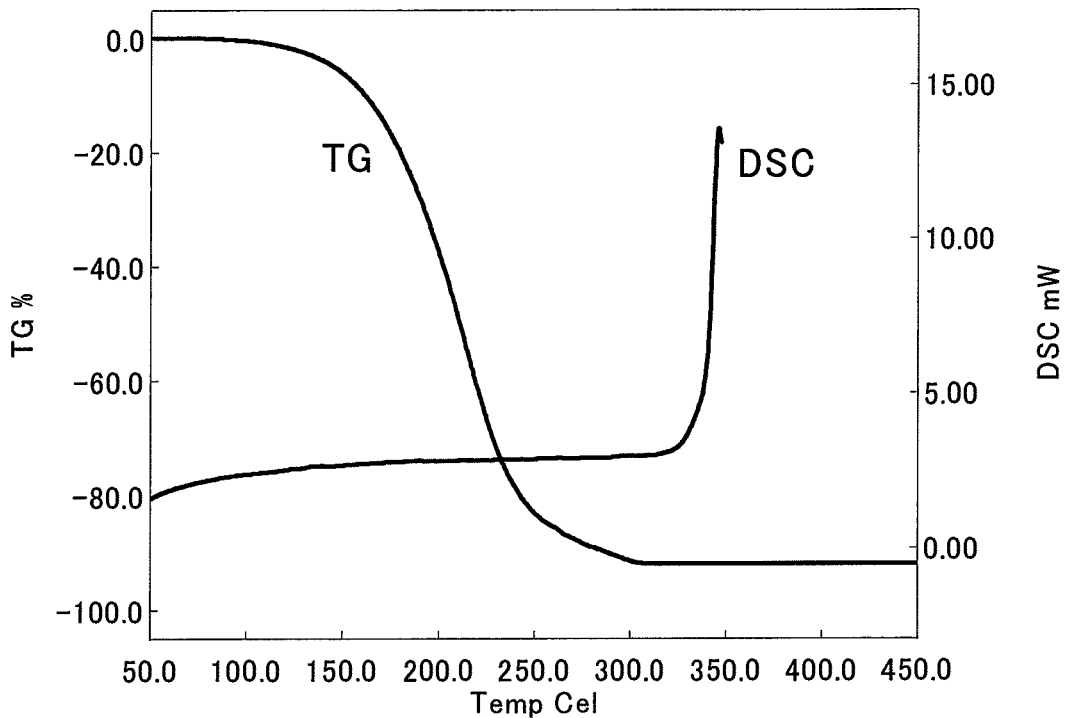
FIG. 10 is a presentation showing the results of the TG and DSC analyses conducted in Test Example 10.

In FIG. 10 are shown the results of TG analysis of the Ti($^t$PeNCHCHN$^t$Pe)(O$^i$Pr)$_2$, in which a measurement was made under the conditions of a heating rate of 10° C./min in an atmosphere through which argon was continuously passed at 400 mL/min, and the results of DSC analysis of the Ti($^t$-PeNCHCHN$^t$Pe)(O$^i$Pr)$_2$, in which a measurement was made in a sealed container at a heating rate of 10° C./min. It is apparent from the results of TG that the Ti($^t$PeNCHCHN$^t$Pe)(O$^i$Pr)$_2$ has vaporization characteristics that make this complex suitable for use as a material in the CVD method, ALD method, or the like. It is apparent from the results of DSC that the Ti($^t$PeNCHCHN$^t$Pe)(O$^i$Pr)$_2$ has satisfactory thermal stability.

Example 12

In an argon atmosphere, 1.90 g (5.71 mmol) of ethene-1,2-diylbis(tert-pentylamido)bis(dimethylamido)titanium (Ti($^t$PeNCHCHN$^t$Pe)(NMe$_2$)$_2$) was dissolved in 10 mL of hexane, and 687 mg (11.4 mmol) of 2-propanol was added thereto. The resultant mixture was stirred in that atmosphere at room temperature for 3 hours. The solvent was removed from this liquid reaction mixture by distillation at a reduced pressure, and the resultant residue was subjected to vacuum distillation (distillation temperature 95° C./0.06 Torr) to thereby obtain Ti($^t$PeNCHCHN$^t$Pe)(O$^i$Pr)$_2$ as a deep-red liquid (amount obtained, 2.00 g; yield, 96%). The Ti($^t$PeNCHCHN$^t$Pe)(O$^i$Pr)$_2$ thus obtained was examined for $^1$H and $^{13}$C NMR spectra. As a result, these spectra agreed with the spectra of the product obtained in Example 11.

Example 13

In an argon atmosphere, 2.38 g (12.1 mmol) of N,N'-di(tert-pentyl)-1,4-diaza-1,3-butadiene ($^t$PeNCHCHN$^t$Pe) was dissolved in 24 mL of tetrahydrofuran, and 584 mg (25.4 mmol) of sodium was added thereto. The resultant mixture was stirred in that atmosphere at room temperature for 12 hours. A solution prepared by dissolving 3.93 g (11.5 mmol) of tetra(tert-butoxo)titanium (Ti(O$^t$Bu)$_4$) in 12 mL of hexane was added to the liquid reaction mixture, and the resultant mixture was stirred at room temperature for 12 hours. The solvent was removed from this liquid reaction mixture by distillation at a reduced pressure, and 25 mL of hexane was added to the residue. The insoluble matter generated was taken out by filtration, and the solvent was removed from the filtrate by distillation at a reduced pressure. The resultant residue was subjected to vacuum distillation (distillation temperature 105° C./0.10 Torr) to thereby obtain ethene-1,2-diylbis(tert-pentylamido)di(tert-butoxo)titanium (Ti($^t$PeNCHCHN$^t$Pe)(O$^t$Bu)$_2$) as a deep-red liquid (amount obtained, 4.28 g; yield, 95%).

$^1$H NMR (500 MHz, C$_6$D$_6$, δ/ppm) 5.87 (s, 2H), 1.58 (q, J=8 Hz, 4H), 1.27 (s, 12H), 1.0-1.7 (br, 18H), 0.81 (t, J=8 Hz, 6H)

$^{13}$C NMR (125 MHz, C$_6$D$_6$, δ/ppm) 103.1, 79.3 (br), 60.0, 37.0, 33.4, 29.4 (br), 9.4.

Test Example 11

Thermal Analyses of Ti($^t$PeNCHCHN$^t$Pe)(O$^t$Bu)$_2$

Figure 11:
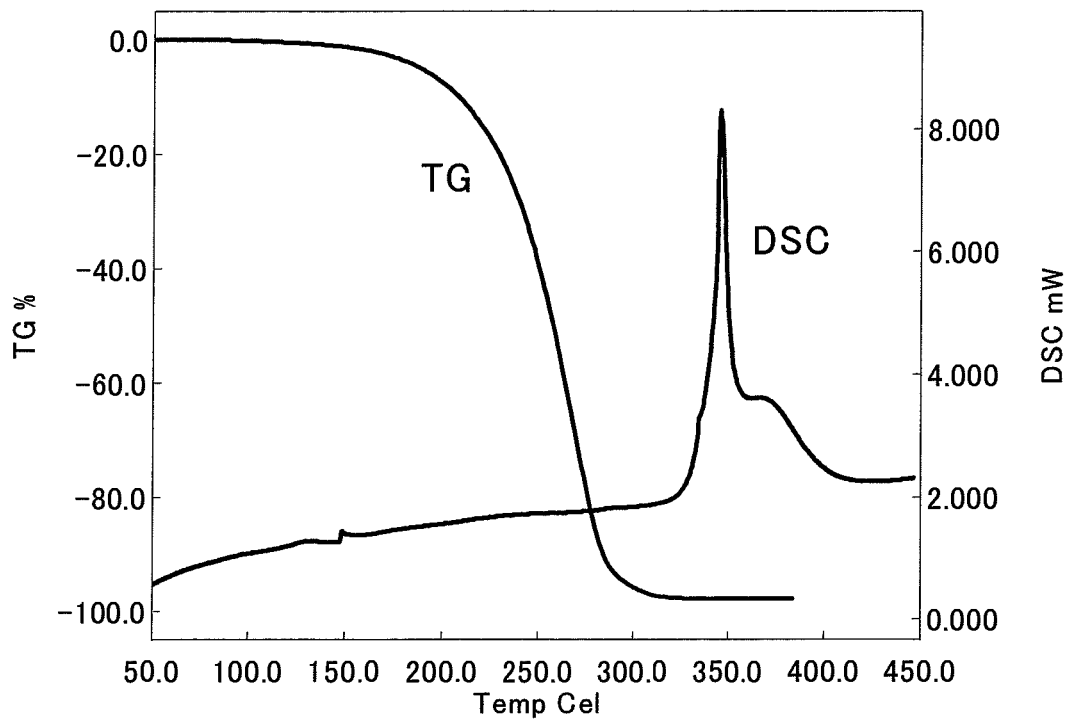
FIG. 11 is a presentation showing the results of the TG and DSC analyses conducted in Test Example 11.

In FIG. 11 are shown the results of TG analysis of the Ti($^t$PeNCHCHN$^t$Pe)(O$^t$Bu)$_2$, in which a measurement was made under the conditions of a heating rate of 10° C./min in an atmosphere through which argon was continuously passed at 400 mL/min, and the results of DSC analysis of the Ti($^t$-PeNCHCHN$^t$Pe)(O$^t$Bu)$_2$, in which a measurement was made in a sealed container at a heating rate of 10° C./min. It is apparent from the results of TG that the Ti($^t$PeNCHCHN$^t$Pe)(O$^t$Bu)$_2$ has vaporization characteristics that make this complex suitable for use as a material in the CVD method, ALD method, or the like. It is apparent from the results of DSC that the Ti($^t$PeNCHCHN$^t$Pe)(O$^t$Bu)$_2$ has satisfactory thermal stability.

Example 14

In an argon atmosphere, 1.10 g (3.32 mmol) of Ti($^t$PeNCHCHN$^t$Pe)(NMe$_2$)$_2$ was dissolved in 5 mL of hexane, and 493 mg (6.65 mmol) of tert-butanol was added thereto. The resultant mixture was stirred in that atmosphere at room temperature for 14 hours. The solvent was removed from this liquid reaction mixture by distillation at a reduced pressure, and the resultant residue was subjected to vacuum distillation (distillation temperature 105° C./0.10 Torr) to thereby obtain Ti($^t$PeNCHCHN$^t$Pe)(O$^t$Bu)$_2$ as a deep-red liquid (amount obtained, 1.24 g; yield, 96%). The Ti($^t$PeNCHCHN$^t$Pe)(O$^t$Bu)$_2$ thus obtained was examined for $^1$H and $^{13}$C NMR spectra. As a result, these spectra agreed with the spectra of the product obtained in Example 13.

Reference Example 2

To a liquid mixture of 19.5 g (151 mmol) of 1,1,3,3-tetramethylbutylamine and 100 mL of water was added 10.7 g (73.5 mmol) of 40% aqueous glyoxal solution. The resultant mixture was stirred at room temperature for 1 hour. The solid yielded was taken out by filtration, washed twice with 10 mL of water, and then dried at a reduced pressure to thereby obtain N,N'-di(1,1,3,3-tetramethylbutyl)-1,4-diaza-1,3-butadiene (Me$_3$CCH$_2$CMe$_2$NCHCHNCMe$_2$CH$_2$CMe$_3$) as a white solid (amount obtained, 19.5 g; yield, 95%).

$^1$H NMR (500 MHz, C$_6$D$_6$, δ/ppm) 8.09 (s, 21-1), 1.61 (s, 41-1), 1.14 (s, 12H), 0.98 (18H)

$^{13}$C NMR (125 MHz, C$_6$D$_6$, δ/ppm) 157.8, 62.0, 56.6, 32.5, 32.2, 29.8.

Example 15

In an argon atmosphere, 2.98 g (10.6 mmol) of Me$_3$CCH$_2$CMe$_2$NCHCHNCMe$_2$CH$_2$CMe$_3$ was dissolved in 30 mL of tetrahydrofuran, and 538 mg (23.4 mmol) of sodium was added thereto. The resultant mixture was stirred in that atmosphere at room temperature for 16 hours. A solution prepared by dissolving 3.02 g (10.6 mmol) of Ti(O$^i$Pr)$_4$ in 15 mL of hexane was added to the liquid reaction mixture, and the resultant mixture was stirred at room temperature for 12 hours. The solvent was removed from this liquid reaction mixture by distillation at a reduced pressure, and 25 mL of hexane was added to the residue. The insoluble matter generated was taken out by filtration, and the solvent was removed from the filtrate by distillation at a reduced pressure. The resultant residue was subjected to vacuum distillation (distillation temperature 130° C./0.04 Torr) to thereby obtain ethene-1,2-diylbis(1,1,3,3-tetramethylbutylamido)diisopropoxotitanium (Ti(Me₃CCH₂CMe₂NCHCHNCMe₂CH₂CMe₃)(O$^i$Pr)₂) as a deep-red liquid (amount obtained, 4.18 g; yield, 88%).

$^1$H NMR (500 MHz, C₆D₆, δ/ppm) 5.93 (s, 2H), 4.83 (br, 1H), 4.11 (br, 1H), 1.62 (s, 4H), 1.2-1.7 (br, 18H), 0.9-1.2 (br, 6H), 0.94 (s, 18H)

$^{13}$C NMR (125 MHz, C₆D₆, δ/ppm) 102.3, 76.0 (br), 73.1 (br), 61.5, 56.9, 32.1, 32.0, 31.9 (br), 27.9.

Test Example 12

Thermal Analyses of
Ti(Me₃CCH₂CMe₂NCHCHNCMe₂CH₂CMe₃)(O$^i$Pr)₂

Figure 12:
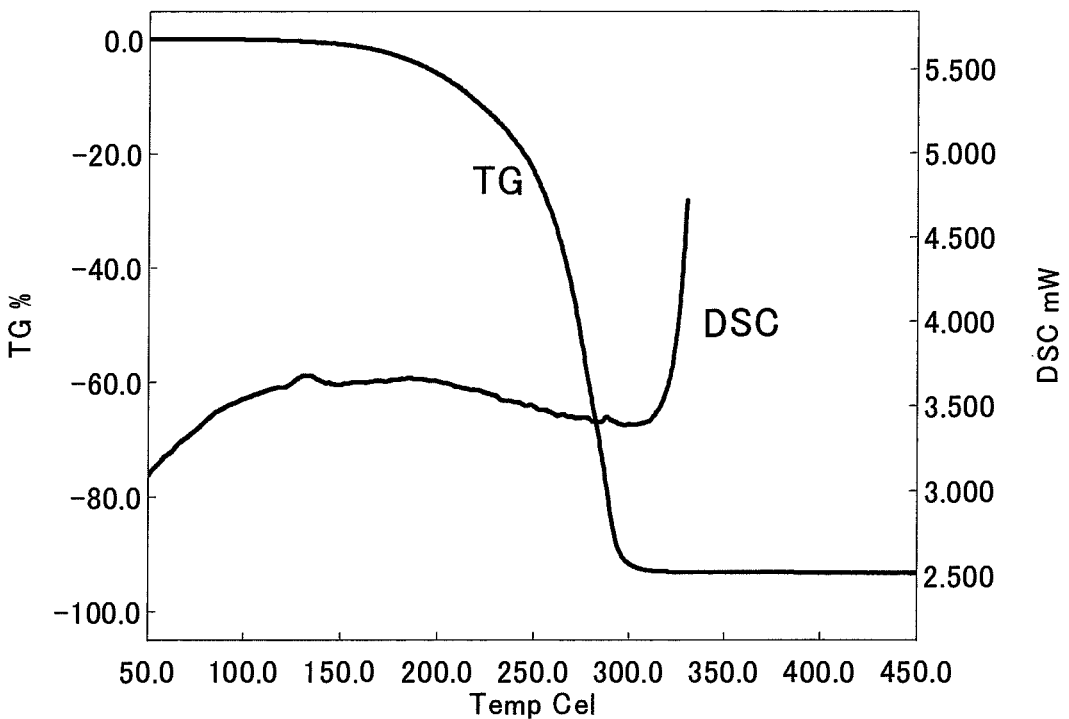
FIG. 12 is a presentation showing the results of the TG and DSC analyses conducted in Test Example 12.

In FIG. 12 are shown the results of TG analysis of the Ti(Me₃CCH₂CMe₂NCHCHNCMe₂CH₂CMe₃)(O$^i$Pr)₂, in which a measurement was made under the conditions of a heating rate of 10° C./min in an atmosphere through which argon was continuously passed at 400 mL/min, and the results of DSC analysis of the Ti(Me₃CCH₂CMe₂NCHCHNCMe₂CH₂CMe₃)(O$^i$Pr)₂, in which a measurement was made in a sealed container at a heating rate of 10° C./min. It is apparent from the results of TG that the Ti(Me₃CCH₂CMe₂NCHCHNCMe₂CH₂CMe₃)(O$^i$Pr)₂ has vaporization characteristics that make this complex suitable for use as a material in the CVD method, ALD method, or the like. It is apparent from the results of DSC that the Ti(Me₃CCH₂CMe₂NCHCHNCMe₂CH₂CMe₃)(O$^i$Pr)₂ has satisfactory thermal stability.

Example 16

Figure 13:
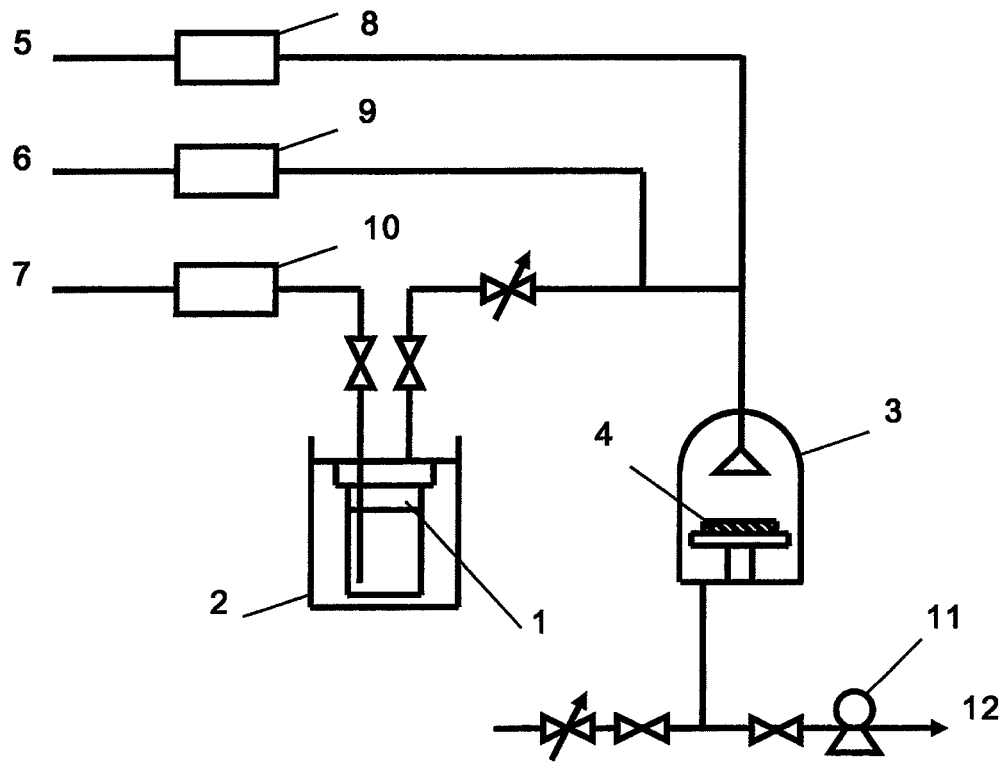
FIG. 13 is a diagrammatic view of the CVD film forming apparatus used in Examples 16 and 17.

Argon as a carrier gas was bubbled, at a flow rate of 30 sccm, into Ti($^t$BuNCHCHN$^t$Bu)(O$^i$Pr)₂ held in a material container kept at 61° C. with a thermostatic bath, and the Ti($^t$BuNCHCHN$^t$Bu)(O$^i$Pr)₂ was thereby vaporized and fed to a reaction chamber. During this operation, the internal pressure of the raw-material container was 100 Torr. Simultaneously with the feeding, argon as a diluent gas and oxygen gas as a reactant gas were supplied to the reaction chamber at flow rates of 180 sccm and 90 sccm, respectively. The temperature of an SiO₂/Si substrate disposed in the reaction chamber was kept at 400° C., and the reaction chamber was evacuated so that the internal pressure thereof was kept at 4 Torr. Under these conditions, a thin film was formed over 1 hour. The CVD film forming apparatus is diagrammatically shown in FIG. 13. The thin film obtained was analyzed with a fluorescent X-ray apparatus and, as a result, the thin film was ascertained to contain Ti. Furthermore, this thin film was analyzed for composition by X-ray photoelectron spectroscopy and, as a result, the thin film was ascertained to be titanium oxide.

Example 17

Argon as a carrier gas was bubbled, at a flow rate of 30 sccm, into Ti($^t$BuNCHCHN$^t$Bu)(O$^i$Pr)₂ held in a material container kept at 61° C. with a thermostatic bath, and the Ti($^t$BuNCHCHN$^t$Bu)(O$^i$Pr)₂ was thereby vaporized and fed to a reaction chamber. During this operation, the internal pressure of the raw-material container was 100 Torr. Simultaneously with the feeding, argon as a diluent gas and oxygen gas as a reactant gas were supplied to the reaction chamber at flow rates of 180 sccm and 90 sccm, respectively. The temperature of an SiO₂/Si substrate disposed in the reaction chamber was kept at 240° C., and the reaction chamber was evacuated so that the internal pressure thereof was kept at 4 Torr. Under these conditions, a thin film was formed over 1 hour. The CVD film forming apparatus is diagrammatically shown in FIG. 13. The thin film obtained was analyzed with a fluorescent X-ray apparatus and, as a result, the thin film was ascertained to contain Ti. Furthermore, this thin film was analyzed for composition by X-ray photoelectron spectroscopy and, as a result, the thin film was ascertained to be titanium oxide.

Example 18

In an argon atmosphere, 28.54 g (93.8 mmol) of Ti($^t$BuNCHCHN$^t$Bu)(NMe₂)₂ was dissolved in 60 mL of hexane, and 13.90 g (187.5 mmol) of sec-butanol was added thereto. The resultant mixture was stirred in that atmosphere at room temperature for 5 hours. The solvent was removed from this liquid reaction mixture by distillation at a reduced pressure, and the resultant residue was subjected to vacuum distillation (distillation temperature 92-96° C./0.03 Torr) to thereby obtain ethene-1,2-diylbis(tert-butylamido)bis(sec-butoxo)titanium (Ti($^t$BuNCHCHN$^t$Bu)(O$^s$Bu)₂) as a deep-red liquid (amount obtained, 32.35 g; yield, 95%). This product is a mixture of isomers based on a difference in chirality involving each sec-butyl group.

$^1$H NMR (500 MHz, C₆D₆, δ/ppm) 5.96 (s, 2H), 4.25 (br, 2H), 1.7-1.3 (br, 4H), 1.30 (s, 18H), 1.3-1.1 (br, 6H), 1.1-0.9 (br, 6H)

$^{13}$C NMR (125 MHz, C₆D₆, δ/ppm) 102.73, 102.71, 102.70, 80.0 (br), 57.8, 57.74, 57.71, 34.3, 31.7, 25.7, 11.1.

Test Example 13

Thermal Analyses of Ti($^t$BuNCHCHN$^t$Bu)(O$^s$Bu)₂

Figure 14:
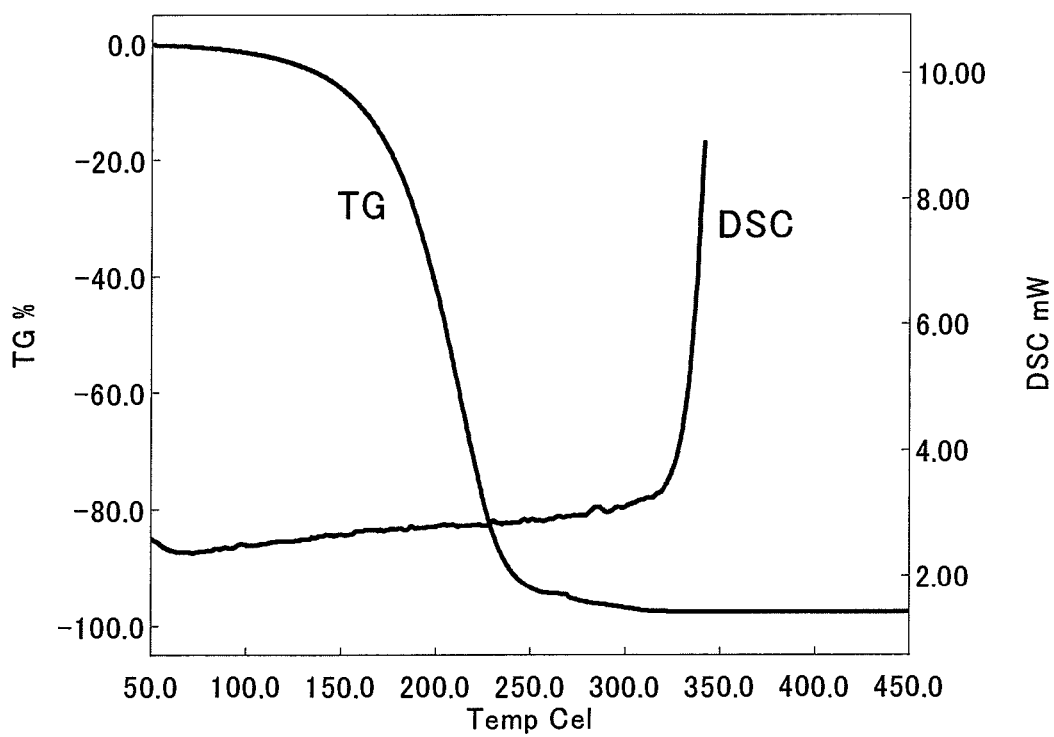
FIG. 14 is a presentation showing the results of the TG and DSC analyses conducted in Test Example 13.

In FIG. 14 are shown the results of TG analysis of the Ti($^t$BuNCHCHN$^t$Bu)(O$^s$Bu)₂, in which a measurement was made under the conditions of a heating rate of 10° C./min in an atmosphere through which argon was continuously passed at 400 mL/min, and the results of DSC analysis of the Ti($^t$BuNCHCHN$^t$Bu)(O$^s$Bu)₂, in which a measurement was made at a heating rate of 10° C./min in a sealed container filled with an argon atmosphere. It is apparent from the results of TG that the Ti($^t$BuNCHCHN$^t$Bu)(O$^s$Bu)₂ has vaporization characteristics that make this complex suitable for use as a material in the CVD method, ALD method, or the like. It is apparent from the results of DSC that the Ti($^t$BuNCHCHN$^t$Bu)(O$^s$Bu)₂ has satisfactory thermal stability.

Example 19

In an argon atmosphere, 14.85 g (88.2 mmol) of N,N'-di(tert-butyl)-1,4-diaza-1,3-butadiene ($^t$BuNCHCHN$^t$Bu) was dissolved in 110 mL of tetrahydrofuran, and 4.18 g (182 mmol) of sodium was added thereto. The resultant mixture was stirred in that atmosphere at room temperature for 14 hours. This liquid reaction mixture was added to a solution prepared by dissolving 29.18 g (85.7 mmol) of tetra-sec-butoxotitanium (Ti(O$^s$Bu)₄) in 50 mL of hexane, and the resultant mixture was stirred at room temperature for 14 hours. The solvent was removed from this liquid reaction mixture by distillation at a reduced pressure, and 120 mL of hexane was added to the residue. The insoluble matter generated was taken out by filtration, and the solvent was removed from the filtrate by distillation at a reduced pressure. The resultant residue was subjected to vacuum distillation (distillation temperature 92-96° C./0.03 Torr) to thereby obtain Ti($^t$BuNCHCHN$^t$Bu)(O$^s$Bu)$_2$ as a deep-red liquid (amount obtained, 28.81 g; yield, 93%). This product is a mixture of isomers based on a difference in chirality involving each sec-butyl group. The Ti($^t$BuNCHCHN$^t$Bu)(O$^s$Bu)$_2$ thus obtained was examined for $^1$H and $^{13}$C NMR spectra. As a result, these spectra agreed with the spectra of the product obtained in Example 18.

Example 20

Figure 15:
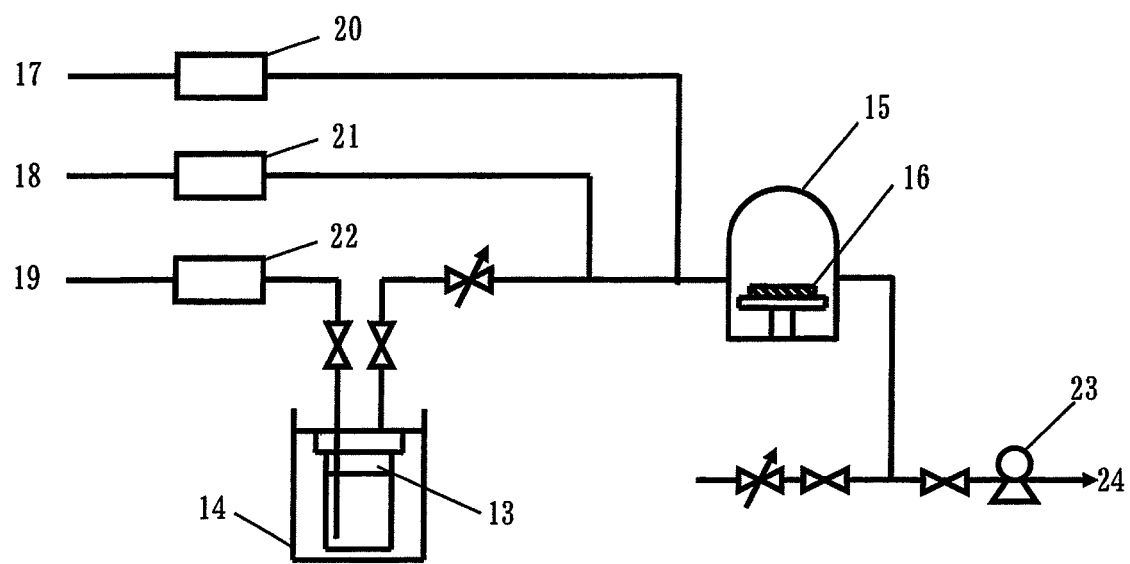
FIG. 15 is a diagrammatic view of the CVD film forming apparatus used in Examples 20, 21, 22, and 23.

Argon as a carrier gas was bubbled, at a flow rate of 10 sccm, into Ti($^t$BuNCHCHN$^t$Bu)(OEt)$_2$ held in a material container kept at 84° C. with a thermostatic bath, and the Ti($^t$BuNCHCHN$^t$Bu)(OEt)$_2$ was thereby vaporized and fed to a reaction chamber. During this operation, the internal pressure of the raw-material container was 100 Torr. Simultaneously with the feeding, argon as a diluent gas and oxygen gas as a reactant gas were supplied to the reaction chamber at flow rates of 230 sccm and 60 sccm, respectively. The temperature of an SiO$_2$/Si substrate disposed in the reaction chamber was kept at 400° C., and the reaction chamber was evacuated so that the internal pressure thereof was kept at 4 Torr. Under these conditions, a thin film was formed over 1 hour. The CVD film forming apparatus is diagrammatically shown in FIG. 15. The thin film obtained was analyzed with a fluorescent X-ray apparatus and, as a result, the thin film was ascertained to contain Ti.

Example 21

Argon as a carrier gas was bubbled, at a flow rate of 10 sccm, into Ti($^t$BuNCHCHN$^t$Bu)(O$^t$Pe)$_2$ held in a material container kept at 84° C. with a thermostatic bath, and the Ti($^t$BuNCHCHN$^t$Bu)(O$^t$Pe)$_2$ was thereby vaporized and fed to a reaction chamber. During this operation, the internal pressure of the raw-material container was 100 Torr. Simultaneously with the feeding, argon as a diluent gas and oxygen gas as a reactant gas were supplied to the reaction chamber at flow rates of 230 sccm and 60 sccm, respectively. The temperature of an SiO$_2$/Si substrate disposed in the reaction chamber was kept at 400° C., and the reaction chamber was evacuated so that the internal pressure thereof was kept at 100 Torr. Under these conditions, a thin film was formed over 1 hour. The CVD film forming apparatus is diagrammatically shown in FIG. 15. The thin film obtained was analyzed with a fluorescent X-ray apparatus and, as a result, the thin film was ascertained to contain Ti.

Example 22

Argon as a carrier gas was bubbled, at a flow rate of 10 sccm, into Ti($^t$PeNCHCHN$^t$Pe)(O$^i$Pr)$_2$ held in a material container kept at 84° C. with a thermostatic bath, and the Ti($^t$PeNCHCHN$^t$Pe)(O$^i$Pr)$_2$ was thereby vaporized and fed to a reaction chamber. During this operation, the internal pressure of the raw-material container was 100 Torr. Simultaneously with the feeding, argon as a diluent gas and oxygen gas as a reactant gas were supplied to the reaction chamber at flow rates of 230 sccm and 60 sccm, respectively. The temperature of an SiO$_2$/Si substrate disposed in the reaction chamber was kept at 400° C., and the reaction chamber was evacuated so that the internal pressure thereof was kept at 4 Torr. Under these conditions, a thin film was formed over 1 hour. The CVD film forming apparatus is diagrammatically shown in FIG. 15. The thin film obtained was analyzed with a fluorescent X-ray apparatus and, as a result, the thin film was ascertained to contain Ti.

Example 23

Argon as a carrier gas was bubbled, at a flow rate of 10 sccm, into Ti($^t$BuNCHCHN$^t$Bu)(O$^s$Bu)$_2$ held in a material container kept at 84° C. with a thermostatic bath, and the Ti($^t$BuNCHCHN$^t$Bu)(O$^s$Bu)$_2$ was thereby vaporized and fed to a reaction chamber. During this operation, the internal pressure of the raw-material container was 100 Torr. Simultaneously with the feeding, argon as a diluent gas and oxygen gas as a reactant gas were supplied to the reaction chamber at flow rates of 230 sccm and 60 sccm, respectively. The temperature of an SiO$_2$/Si substrate disposed in the reaction chamber was kept at 400° C., and the reaction chamber was evacuated so that the internal pressure thereof was kept at 4 Torr. Under these conditions, a thin film was formed over 1 hour. The CVD film forming apparatus is diagrammatically shown in FIG. 15. The thin film obtained was analyzed with a fluorescent X-ray apparatus and, as a result, the thin film was ascertained to contain Ti.

While the invention has been described in detail and with reference to specific embodiments thereof, it will be apparent to one skilled in the art that various changes and modifications can be made therein without departing from the spirit and scope thereof.

This application is based on a Japanese patent application filed on Jun. 23, 2008 (Application No. 2008-163477) and a Japanese patent application filed on May 26, 2009 (Application No. 2009-126417), the contents thereof being incorporated herein by reference.

INDUSTRIAL APPLICABILITY

The titanium complex (1) of the invention has satisfactory vaporization characteristics and excellent thermal stability, namely, has a high vapor pressure and high thermal stability, and can be used as a material to produce a titanium-containing thin film by a technique such as the CVD method or ALD method. Consequently, the invention has a remarkable industrial value.

| DESCRIPTION OF REFERENCE NUMERALS | |
|---|---|
| 1. | Material container |
| 2. | Thermostatic bath |
| 3. | Reaction chamber |
| 4. | Substrate |
| 5. | Reactant gas |
| 6. | Diluent gas |
| 7. | Carrier gas |
| 8. | Mass flow controller |
| 9. | Mass flow controller |
| 10. | Mass flow controller |
| 11. | Vacuum pump |
| 12. | Exhaust |
| 13. | Material container |
| 14. | Thermostatic bath |
| 15. | Reaction chamber |
| 16. | Substrate |
| 17. | Reactant gas |
| 18. | Diluent gas |
| 19. | Carrier gas |
| 20. | Mass flow controller |
| 21. | Mass flow controller |
| 22. | Mass flow controller |
| 23. | Vacuum pump |
| 24. | Exhaust |

The invention claimed is:

1. A titanium complex of ethene-1,2,diylbis(tert-butylamido)diisopropoxotitanium, ethene-1,2-diylbis(tert-butylamido)bis(tert-pentyloxo)titanium, or ethene-1,2-diylbis(tert-pentylamido)diisopropoxotitanium, wherein said titanium complex is in a liquid form.

2. A process for producing a titanium complex represented by general formula (1):

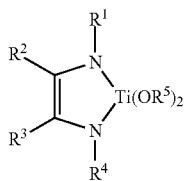
(1)

(wherein $R^1$ and $R^4$ each independently represent an alkyl group having 1-16 carbon atoms; $R^2$ and $R^3$ each independently represent a hydrogen atom or an alkyl group having 1-3 carbon atoms; and $R^5$ represents an alkyl group which has 1-16 carbon atoms and is optionally substituted with one or more fluorine atoms), characterized by subjecting a diimine represented by general formula (2):

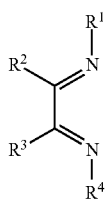
(2)

(wherein $R^1$ and $R^4$ each independently represent an alkyl group having 1-16 carbon atoms, and $R^2$ and $R^3$ each independently represent a hydrogen atom or an alkyl group having 1-3 carbon atoms), an alkali metal, and an alkoxo complex represented by general formula (3):

$$Ti(OR^5)_4 \qquad (3)$$

(wherein $R^5$ represents an alkyl group which has 1-16 carbon atoms and is optionally substituted with one or more fluorine atoms) to reaction with one another.

3. The production process as claimed in claim 2, wherein $R^1$ and $R^4$ each independently represent an alkyl group having 2-6 carbon atoms; $R^2$ and $R^3$ represent a hydrogen atom; and $R^5$ represents an alkyl group having 1-8 carbon atoms.

4. The production process as claimed in claim 2, wherein $R^1$ and $R^4$ each independently represent an alkyl group having 4 or 5 carbon atoms; $R^2$ and $R^3$ represent a hydrogen atom; and $R^5$ represents an alkyl group having 3-5 carbon atoms.

5. The production process as claimed in claim 3, wherein $R^1$ and $R^4$ each independently represent an alkyl group having 4 or 5 carbon atoms; $R^2$ and $R^3$ represent a hydrogen atom; and $R^5$ represents an alkyl group having 3-5 carbon atoms.

6. A process for producing a titanium complex of ethene-1,2-diylbis(tert-butylamido)diisopropoxotitanium, ethene-1,2-diylbis(tert-butylamido)bis(tert-pentyloxo)titanium, or ethene-1,2-diylbis(tert-pentylamido)diisopropoxotitanium, comprising subjecting an alcohol represented by general formula (5):

$$R^{5a}OH \qquad (5)$$

(wherein $R^{5a}$ represents tert-butyl or tert-pentyl to a reaction with an amide complex represented by general formula (4):

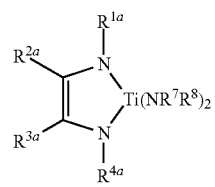
(4)

(wherein $R^{1a}$ and $R^{4a}$ are the same and represent tert-butyl or tert-pentyl; $R^{2a}$ and $R^{3a}$ represent a hydrogen atom; and $R^7$ and $R^8$ each independently represent an alkyl group which has 1-4 carbon atoms and is optionally substituted with one or more fluorine atoms), wherein said titanium complex is in a liquid form.

7. A process for producing a titanium-containing thin film, characterized by decomposing a titanium complex represented by general formula (1) as a material on a substrate:

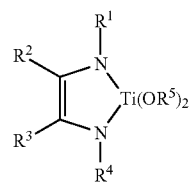
(1)

(wherein $R^1$ and $R^4$ each independently represent an alkyl group having 1-16 carbon atoms; $R^2$ and $R^3$ each independently represent a hydrogen atom or an alkyl group having 1-3 carbon atoms; and $R^5$ represents an alkyl group which has 1-16 carbon atoms and is optionally substituted with one or more fluorine atoms), wherein said titanium complex is in a liquid form.

* * * * *